United States Patent
Ohno et al.

(10) Patent No.: US 10,503,958 B2
(45) Date of Patent: Dec. 10, 2019

(54) LIVING BODY DETERMINATION DEVICE, LIVING BODY DETERMINATION METHOD, AND PROGRAM

(71) Applicant: NEC Corporation, Minato-ku, Tokyo (JP)

(72) Inventors: Yuji Ohno, Tokyo (JP); Masahiro Kubo, Tokyo (JP); Katsumi Abe, Tokyo (JP); Kimiyasu Takoh, Tokyo (JP); Ersin Altintas, Tokyo (JP); Takeshi Akagawa, Tokyo (JP); Tetsuri Ariyama, Tokyo (JP); Ichiro Ishimaru, Kagawa (JP)

(73) Assignee: NEC CORPORATION, Tokyo (JP)

( * ) Notice: Subject to any disclaimer, the term of this patent is extended or adjusted under 35 U.S.C. 154(b) by 78 days.

(21) Appl. No.: 15/759,880

(22) PCT Filed: Sep. 9, 2016

(86) PCT No.: PCT/JP2016/076670
§ 371 (c)(1),
(2) Date: Mar. 14, 2018

(87) PCT Pub. No.: WO2017/047525
PCT Pub. Date: Mar. 23, 2017

(65) Prior Publication Data
US 2018/0239944 A1 Aug. 23, 2018

(30) Foreign Application Priority Data

Sep. 17, 2015 (JP) ................................. 2015-184188

(51) Int. Cl.
*G06K 9/00* (2006.01)
*A61B 5/1172* (2016.01)
(Continued)

(52) U.S. Cl.
CPC .......... *G06K 9/0012* (2013.01); *A61B 5/0075* (2013.01); *A61B 5/1172* (2013.01);
(Continued)

(58) Field of Classification Search
CPC ....... G06K 9/0012; G06K 2009/00932; G06K 9/00013; G06K 9/00087;
(Continued)

(56) References Cited

U.S. PATENT DOCUMENTS 8,861,808 B2 * 10/2014 Kulcke ................ G06K 9/0012
356/71
2007/0253607 A1 * 11/2007 Higuchi ............. G06K 9/00026
382/124

(Continued)

FOREIGN PATENT DOCUMENTS

JP   2007-122237 A   5/2007
JP   2009-544108 A   12/2009
(Continued)

OTHER PUBLICATIONS

International Search Report for PCT Application No. PCT/JP2016/076670, dated Dec. 13, 2016.

*Primary Examiner* — Li Liu

(57) ABSTRACT

A living body is accurately determined while minimizing increases in the size of a device and increases in the number of components. A living body determination device includes a spectroscopic device 104 that disperses light entering from a pedestal side and outputs the result; a light emission device 101 that emits first light toward the pedestal from a position facing the spectroscopic device 104 with the pedestal therebetween; a light emission device 102 that emits second light toward the pedestal from the spectroscopic device 104 side; an image acquisition device 105 that outputs image information indicating a brightness corresponding to the intensity of the light output by the spectroscopic device 104;

(Continued)

and a calculation device 106 that acquires first image information regarding each of the spectra of the first light from the image acquisition device 105, acquires first spectroscopic information on the basis of each of the pieces of first image information, acquires second image information regarding each of the spectra of the second light from the image acquisition device 105, acquires second spectroscopic information on the basis of each of the pieces of second image information, and determines whether or not a measurement target 10a is a living body, based on the first and second spectroscopic information.

12 Claims, 26 Drawing Sheets

(51) Int. Cl.
*A61B 5/00* (2006.01)
*G01J 3/28* (2006.01)
*G01J 3/447* (2006.01)
*G06K 9/20* (2006.01)

(52) U.S. Cl.
CPC ............ *A61B 5/489* (2013.01); *G01J 3/2823* (2013.01); *G01J 3/447* (2013.01); *G06K 9/00033* (2013.01); *G06K 9/00087* (2013.01); *G06K 9/2018* (2013.01)

(58) Field of Classification Search
CPC ....... G06K 2009/0006; G06K 9/00906; G06K 9/2027; A61B 5/1172; A61B 5/489; A61B 5/0075; G06F 21/32
See application file for complete search history.

(56) References Cited

U.S. PATENT DOCUMENTS

| | | | |
|---|---|---|---|
| 2008/0192988 A1 | 8/2008 | Uludag et al. | |
| 2009/0232362 A1* | 9/2009 | Otsubo | G06K 9/00026 382/115 |
| 2009/0232367 A1 | 9/2009 | Shinzaki | |
| 2009/0304237 A1* | 12/2009 | Yoshikawa | A61B 5/1172 382/116 |
| 2010/0008544 A1* | 1/2010 | Abe | G06F 21/32 382/115 |
| 2010/0141380 A1* | 6/2010 | Pishva | G06K 9/0012 340/5.2 |
| 2011/0230769 A1* | 9/2011 | Yamazaki | G06K 9/00362 600/473 |
| 2011/0242304 A1* | 10/2011 | Ichige | G06K 9/00107 348/77 |
| 2012/0070043 A1* | 3/2012 | Higuchi | A61B 5/1172 382/124 |
| 2012/0114195 A1* | 5/2012 | Matsuda | G06K 9/00013 382/115 |
| 2013/0329031 A1* | 12/2013 | Miura | G06K 9/00013 348/77 |
| 2016/0256079 A1* | 9/2016 | Shimano | G06K 9/00013 |

FOREIGN PATENT DOCUMENTS

| | | |
|---|---|---|
| JP | 1468896 B2 | 5/2010 |
| JP | 1567479 B2 | 10/2010 |
| JP | 2010-282519 A | 12/2010 |
| JP | 1844939 B2 | 12/2011 |

* cited by examiner

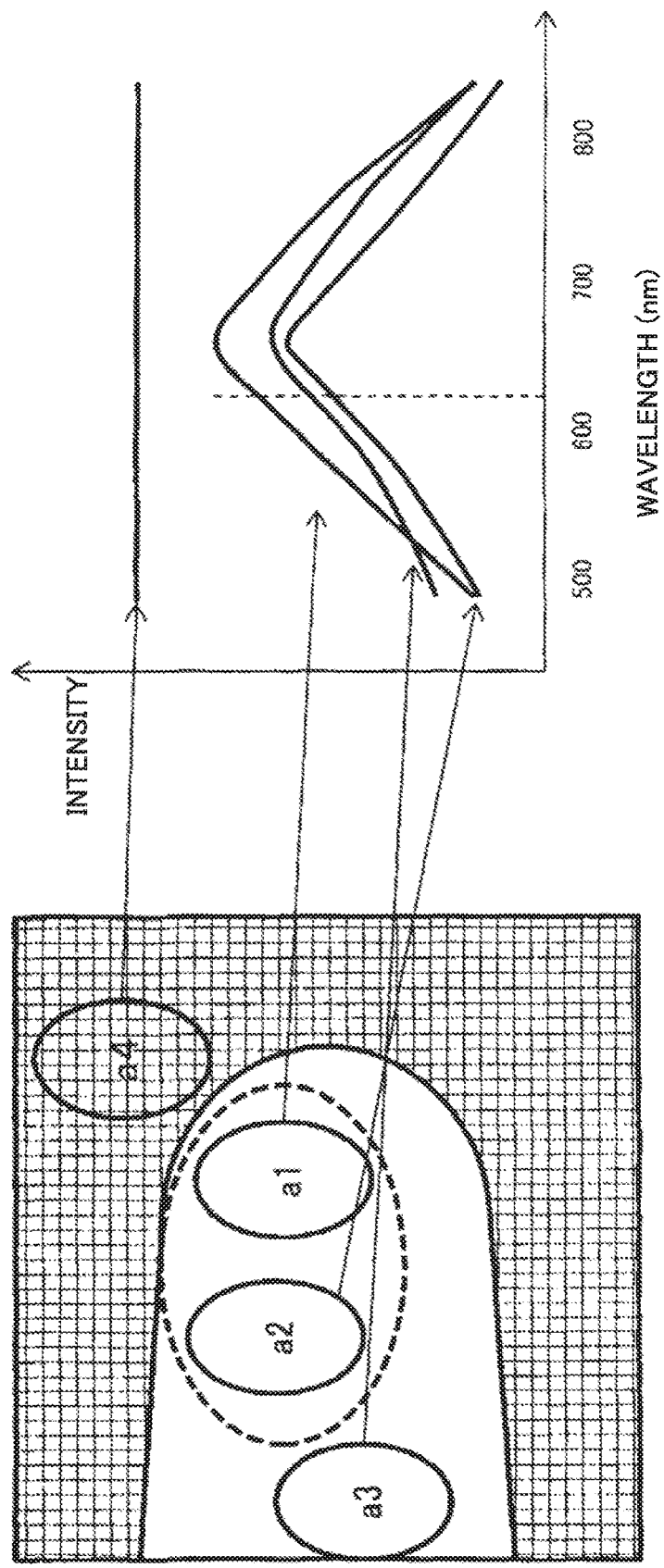

LIVING BODY DETERMINATION DEVICE, LIVING BODY DETERMINATION METHOD, AND PROGRAM

This application is a National Stage Entry of PCT/JP2016/076670 filed on Sep. 9, 2016, which claims priority from Japanese Patent Application 2015-184188 filed on Sep. 17, 2015, the contents of all of which are incorporated herein by reference, in their entirety.

TECHNICAL FIELD

The present invention relates to a living body determination device, a living body determination method, and a program for determining whether or not a measurement target is a living body. The present invention also relates to a biometric authentication device, a biometric authentication method, and a program to which such living body determination is applied.

BACKGROUND ART

In recent years, there have been provided various devices and systems having a biometric authentication function for performing biometric authentication with use of biometric information indicating physical features such as fingerprints. However, reliability of biometric authentication was not sufficiently high because there were some cases where a forged physical characteristic (for example, a false finger) was erroneously determined as genuine.

Therefore, as a countermeasure against fraudulent authentication using a false finger or the like, living body determination is being performed to determine whether or not the measurement target is a living body. For example, Patent Documents 1 to 4 disclose devices and systems in which living body determination and biometric authentication are performed.

The biometric information measurement device disclosed in Patent Document 1 includes a fingerprint reading device including an image capturing unit that detects a fingerprint pattern, a measurement unit that measures a blood flow velocity of a measurement target, and a calculation unit that determines, based on the measurement result (Doppler shift associated with blood flow velocity), whether or not the measurement target is a living body. The measurement unit is composed of two ultrasonic wave sensors. Each ultrasonic wave sensor is provided with an ultrasonic wave transmitting device and an ultrasonic wave receiving device.

The authentication device disclosed in Patent Document 2 includes a biometric information input unit that collects a fingerprint image of a finger, and a biometric detection unit that collects a blood vessel pattern in the finger by irradiating light to the finger. Based on the collected blood vessel pattern, it is determined whether or not it is a false finger.

The multifactor authentication system disclosed in Patent Document 3 includes a non-spectroscopic biometric information acquisition device that acquires a fingerprint image by image capturing a finger, and a spectroscopic biometric information acquisition device that acquires a diffuse reflection spectrum from the finger. Based on the diffuse reflection spectrum from the finger it is determined whether or not the authentication target is a living body having a predetermined spectroscopic feature.

The image capturing device for forgery determination disclosed in Patent Document 4 includes an image capturing device, a color detection device, a data recording device, a color determination device, and a control device.

The image capturing device color-image-captures a characteristic portion of a subject with visible light and outputs image data for each of a plurality of color components. The plurality of color components are R (red), G (green), B (blue), and NIR (near-infrared). The color detection device detects the color of the characteristic portion from the image data of each color component from the image capturing device.

The data recording device preliminarily holds identification values for identifying the color of the image data of the characteristic portion of the subject. The color determination device identifies the color of the characteristic portion detected by the color determination device and determines whether or not it conforms, based on the color identification value recorded in the data recording device. When the color of the characteristic portion detected by the color detection device does not conforms with the color of the image data recorded in the data recording device, the control device determines the characteristic portion as a forged object.

PRIOR ART DOCUMENTS

Patent Documents

[Patent Document 1] Japanese Patent No. 4567479
[Patent Document 2] Japanese Patent No. 4468896
[Patent Document 3] Japanese Patent No. 4844939
[Patent Document 4] Japanese Unexamined Patent Application, First Publication No. 2007-122237

DISCLOSURE OF THE INVENTION

Problem to be Solved by the Invention

However, the devices and systems disclosed in Patent Documents 1 to 4 have the following problems.

In the biometric information measurement device described in Patent Document 1, two ultrasonic wave sensors each including the ultrasonic wave transmitting device and the ultrasonic wave receiving device are provided for living body determination separately from the fingerprint reading device. Therefore, the number of components is increased and the device is also increased in size. Also, in an environment where noise unique to ultrasonic waves is likely to occur, blood flow velocity cannot be accurately measured. Therefore, it may be difficult in some cases to accurately determine whether or not the measurement target is a living body.

In the authentication device disclosed in Patent Document 2, in living body determination based on a blood vessel pattern in a finger, for example, there are some cases where a cut finger or a finger with an elaborately forged blood vessel pattern is erroneously determined as a finger of a living body.

In the multifactor authentication system disclosed in Patent Document 3, in living body determination based on diffuse reflection spectrum from a finger, for example, there are some cases where when a film-shaped forged fingerprint is attached to a part of the fingertip, a fragment of the film-shaped forged fingerprint may be overlooked.

In the image capturing device for forgery determination disclosed in Patent Document 4, color information acquired by the image capturing device (the color of the color filter) is at most R (red), G (green), B (blue) and NIR (near-infrared). Hence it is relatively easy to fabricate a forged object that resembles the color of a living body. Therefore, there is a limit to improving the reliability of biometric authentication.

Means for Solving the Problem

An exemplary object of the present invention is to provide a living body determination device, a living body determination method, and a program that solve the above problems, that can accurately perform determination of a living body without an increase in the size of the device and an increase in the number of components, and that are also capable of detecting a film-shaped forged fingerprint fragment.

Another object of the present invention is to provide a biometric authentication device, a biometric authentication method, and a program that are capable of improving the reliability of biometric authentication and ensuring a high level of security.

In order to achieve the above object, according to one exemplary aspect of the present invention, there is provided a living body determination device including:

a pedestal for placing a measurement target;

a spectroscopic means that receives light entering from the pedestal side and disperses the light into intensities corresponding to wavelengths and outputs it;

a first light emission means that is provided at a position facing the spectroscopic means with the pedestal therebetween and emits first light having a plurality of spectra toward the pedestal;

a second light emission means that emits second light having a plurality of spectra toward the pedestal from the spectroscopic means side;

an image acquisition means that receives light output from the spectroscopic means and outputs image information indicating brightness corresponding to an intensity of the light; and a control unit that acquires first image information related to the measurement target from the image acquisition means for each spectrum of the first light and acquires first spectroscopic information based on each first image information, the control unit acquiring second image information related to the measurement target from the image acquisition means for each spectrum of the second light and acquiring second spectroscopic information based on each second image information, and the control unit determining whether or not the measurement target is a living body based on comparison results between each of the first and second spectroscopic information and a predetermined spectral characteristic.

Furthermore, according to another exemplary aspect of the present invention, there is provided a living body determination method that is performed by a device, the device including: a pedestal for placing a measurement target; a spectroscopic means that receives light entering from the pedestal side and disperses the light into intensities corresponding to wavelengths and outputs it; a first light emission means that is provided at a position facing the spectroscopic means with the pedestal therebetween and emits first light having a plurality of spectra toward the pedestal; a second light emission means that emits second light having a plurality of spectra toward the pedestal from the spectroscopic means side; and an image acquisition means that receives light output from the spectroscopic means and outputs image information indicating brightness corresponding to an intensity of the light, the method:

acquiring first image information related to the measurement target from the image acquisition means for each spectrum of the first light and acquiring first spectroscopic information based on each first image information, acquiring second image information related to the measurement target from the image acquisition means for each spectrum of the second light and acquiring second spectroscopic information based on each second image information; and determining whether or not the measurement target is a living body based on comparison results between each of the first and second spectroscopic information and a predetermined spectral characteristic.

Moreover, according to still another exemplary aspect of the present invention, there is provided a program that causes a computer of a device including: a pedestal for placing a measurement target; a spectroscopic means that receives light entering from the pedestal side and disperses the light into intensities corresponding to wavelengths and outputs it; a first light emission means that is provided at a position facing the spectroscopic means with the pedestal therebetween and emits first light having a plurality of spectra toward the pedestal; a second light emission means that emits second light having a plurality of spectra toward the pedestal from the spectroscopic means side; and an image acquisition means that receives light output from the spectroscopic means and outputs image information indicating brightness corresponding to an intensity of the light, to execute:

a process of acquiring first image information related to the measurement target from the image acquisition means for each spectrum of the first light and acquiring first spectroscopic information based on each first image information;

a process of acquiring second image information related to the measurement target from the image acquisition means for each spectrum of the second light and acquiring second spectroscopic information based on each second image information; and a process of determining whether or not the measurement target is a living body based on comparison results between each of the first and second spectroscopic information and a predetermined spectral characteristic.

In order to achieve another object above, according to one exemplary aspect of the present invention, there is provided a biometric authentication device including:

a pedestal for placing a measurement target;

a spectroscopic means that receives light entering from the pedestal side and disperses the light into intensities corresponding to wavelengths and outputs it;

a first light emission means that is provided at a position facing the spectroscopic means with the pedestal therebetween and emits first light having a plurality of spectra toward the pedestal;

a second light emission means that emits second light having a plurality of spectra toward the pedestal from the spectroscopic means side;

an image acquisition means that receives light output from the spectroscopic means and outputs image information indicating brightness corresponding to an intensity of the light; and an image processing unit that acquires first image information related to the measurement target from the image acquisition means for each spectrum of the first light and acquires first spectroscopic information based on each first image information, the image processing unit acquiring second image information related to the measurement target from the image acquisition means for each spectrum of the second light and acquiring, based on each second image information, second spectroscopic information and biometric information, the biometric information indicating depressions and protrusions on a surface of the measurement target;

a living body authenticity determination unit that determines whether or not the measurement target is a living body based on comparison results between each of the first and second spectroscopic information and a predetermined spectral characteristic; and a biometric authentication unit that determines whether or not the biometric information matches preliminarily registered authentication biometric information in a case where the measurement target is determined as a living body, the biometric authentication unit determining a successful authentication in a case where they are matched, and the biometric authentication unit determining an authentication error in a case where they are not matched.

Furthermore, according to another exemplary aspect of the present invention, there is provided a biometric authentication method that is performed by a device, the device including: a pedestal for placing a measurement target; a spectroscopic means that receives light entering from the pedestal side and disperses the light into intensities corresponding to wavelengths and outputs it; a first light emission means that is provided at a position facing the spectroscopic means with the pedestal therebetween and emits first light having a plurality of spectra toward the pedestal; a second light emission means that emits second light having a plurality of spectra toward the pedestal from the spectroscopic means side; and an image acquisition means that receives light output from the spectroscopic means and outputs image information indicating brightness corresponding to an intensity of the light, the method:

acquiring first image information related to the measurement target from the image acquisition means for each spectrum of the first light and acquiring first spectroscopic information based on each first image information;

acquiring second image information related to the measurement target from the image acquisition means for each spectrum of the second light and acquiring, based on each second image information, second spectroscopic information and biometric information, the biometric information indicating depressions and protrusions on a surface of the measurement target;

determining whether or not the measurement target is a living body based on comparison results between each of the first and second spectroscopic information and a predetermined spectral characteristic; and determining whether or not the biometric information matches preliminarily registered authentication biometric information in a case where the measurement target is determined as a living body, determining a successful authentication in a case where they are matched, and determining an authentication error in a case where they are not matched.

Moreover, according to still another exemplary aspect of the present invention, there is provided a program that causes a computer of a device including: a pedestal for placing a measurement target; a spectroscopic means that receives light entering from the pedestal side and disperses the light into intensities corresponding to wavelengths and outputs it; a first light emission means that is provided at a position facing the spectroscopic means with the pedestal therebetween and emits first light having a plurality of spectra toward the pedestal; a second light emission means that emits second light having a plurality of spectra toward the pedestal from the spectroscopic means side; and an image acquisition means that receives light output from the spectroscopic means and outputs image information indicating brightness corresponding to an intensity of the light, to execute:

a process of acquiring first image information related to the measurement target from the image acquisition means for each spectrum of the first light and acquiring first spectroscopic information based on each first image information;

a process of acquiring second image information related to the measurement target from the image acquisition means for each spectrum of the second light and acquiring, based on each second image information, second spectroscopic information and biometric information, the biometric information indicating depressions and protrusions on a surface of the measurement target;

a process of determining whether or not the measurement target is a living body based on comparison results between each of the first and second spectroscopic information and a predetermined spectral characteristic; and a process of determining whether or not the biometric information matches preliminarily registered authentication biometric information in a case where the measurement target is determined as a living body, determining a successful authentication in a case where they are matched, and determining an authentication error in a case where they are not matched.

BRIEF DESCRIPTION OF THE DRAWINGS

FIG. 5 is a diagram for explaining a relationship between image information and spectroscopic information.

EMBODIMENTS FOR CARRYING OUT THE INVENTION

Next, exemplary embodiments of the present invention will be described, with reference to the drawings.

First Exemplary Embodiment

Figure 1:
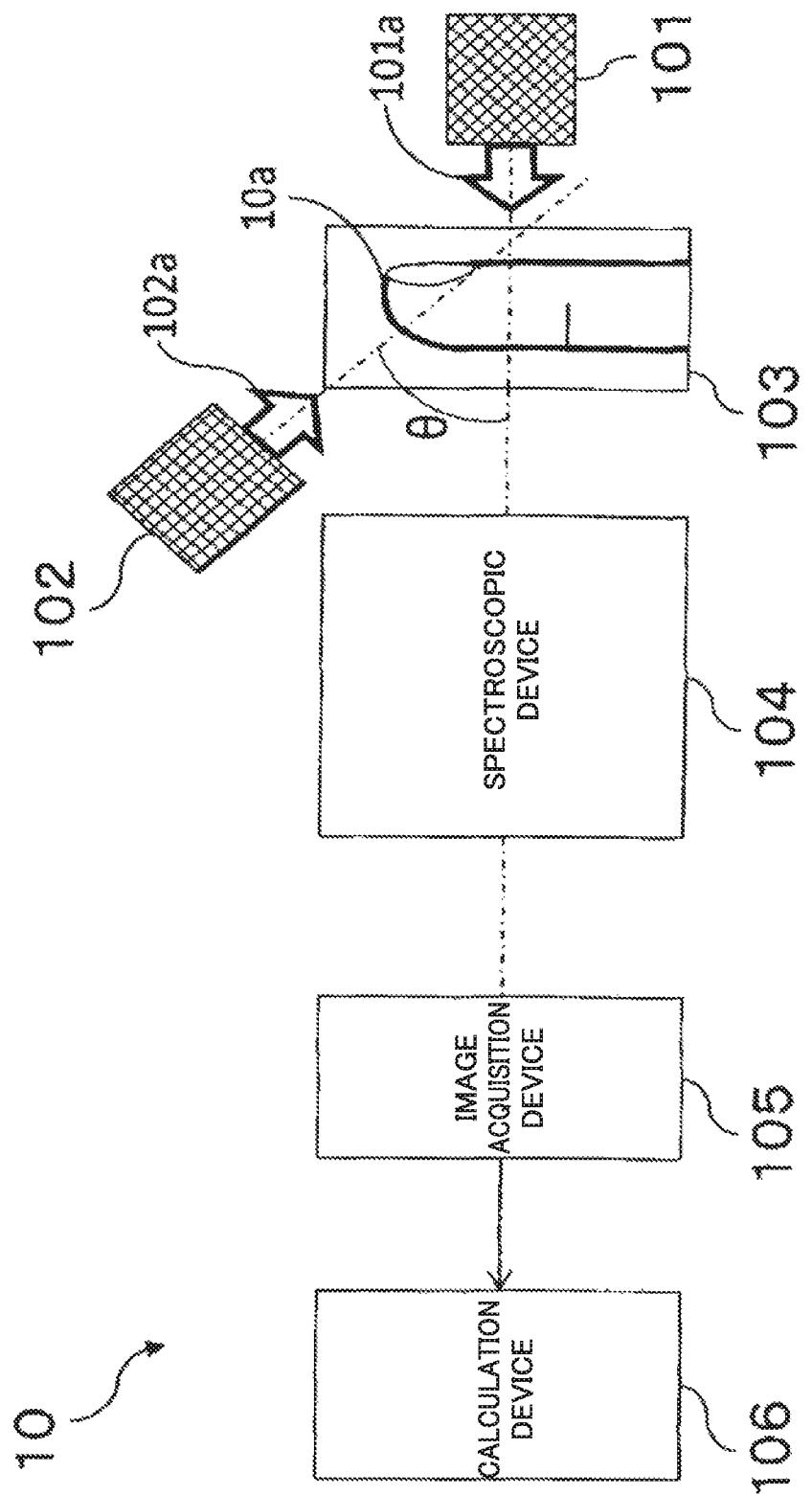
FIG. 1 is a block diagram showing a configuration of a living body determination device according to a first exemplary embodiment of the present invention.

FIG. 1 is a block diagram showing a configuration of a living body determination device according to a first exemplary embodiment of the present invention.

Referring to FIG. 1, a living body determination device 10 has light emission devices 101, 102, a measurement target placement device 103, a spectroscopic device 104, an image acquisition device 105, and a calculation device 106.

The measurement target placement device 103 includes a pedestal for placing a measurement target 10a. Here, the measurement target 10a is a part of a body (for example, a finger or a hand). In FIG. 1, a finger is schematically shown as an example of the measurement target 10a.

The light emission devices 101, 102 emit lights 101a, 102a from mutually different directions toward the pedestal of the measurement target placement device 103. The light emission device 101 is disposed at a position facing the spectroscopic device 104 with the pedestal therebetween. In the case where the pedestal serving as a reference divides the spectroscopic device 104 side and the light emission device 101 side, the light emission device 102 is disposed on the spectroscopic device 104 side. When viewed from the direction perpendicular to the pedestal surface of the measurement target placement device 103, the respective optical axes of the light emission devices 101, 102 intersect with each other at an angle θ, and the spectroscopic device 104 is positioned on the optical axis of the light emission device 101. The angle θ can be appropriately set, but is desirably not more than 90°.

Each of the light emission devices 101, 102 has a light source having a plurality of spectra within a wavelength range from a visible light range to a near-infrared light range, and an optical system for directing the light emitted from the light source toward the pedestal. The visible light range is approximately in a wavelength range from 380 nm to 780 nm, and the near-infrared light range is approximately in a wavelength range from 700 nm to 2500 nm. For example, a white LED combining an LED (Light Emitting Device) and a phosphor, a light source composed of a plurality of LEDs having different light emission wavelengths, a halogen lamp, a xenon lamp, or the like can be used as a light source of the light emission devices 101, 102. Further, as the light source of the light emission devices 101, 102, a light source having an optical filter that transmits only a specific wavelength may be used.

The lights 101a, 102a from the light emission devices 101, 102 are transmitted through the measurement target 10a or are reflected or diffused by the measurement target 10a. As a result, the lights are emitted from the vicinity of the pedestal of the measurement target placement device 103 in various directions. Part of the emitted light (transmitted light, reflected light and diffused light) from the vicinity of the pedestal of the measurement target placement device 103 is directed toward the spectroscopic device 104.

The positions of the light emission devices 101, 102 are not limited to the positions shown in the drawing. For example, the light emission device 101 may be disposed at any position as long as the emitted light passes through the inside of the measurement target 10a and the transmitted light thereof enters the spectroscopic device 104. Moreover, the light emission device 102 may be disposed at any position as long as the emitted light is reflected in the vicinity of the surface of the measurement target 10a and the reflected light thereof enters the spectroscopic device 104.

The spectroscopic device 104 receives light entering from the pedestal side of the measurement target placement device 103 and disperses and outputs the light entered therein into intensities corresponding to wavelengths. The light output from the spectroscopic device 104 is supplied to the image acquisition device 105. As the spectroscopic device 104, for example, a dispersive spectroscope device, a Fourier transform type spectroscopic device, a liquid crystal bandpass filter, or the like can be used.

The Fourier transform type spectroscopic device gives a spatial phase difference to light that enters thereinto and emits an interference wave (interferogram). Specifically, the Fourier transform type spectroscopic device has a phase variable filter (for example, a movable mirror) on the optical Fourier transform plane, and gives spatial phase difference to the light that enters thereinto by operating this phase variable filter. By giving a spatial phase difference to the light that enters thereinto, the imaging state in the image acquisition device 105 changes. The imaging intensity distribution varies according to a given spatial phase difference. Here, by changing the spatial phase difference in a stepwise or continuous manner, an interferogram can be acquired.

Figure 2:
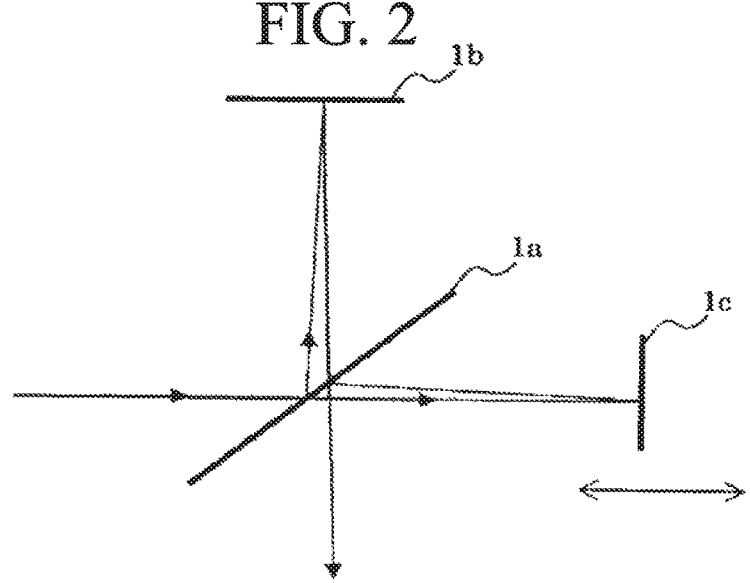
FIG. 2 is a schematic diagram showing a configuration of a Fourier transform type spectroscopic device used in the living body determination device shown in FIG. 1.

FIG. 2 shows an example of a Fourier transform type spectroscopic device. This Fourier transform type spectroscopic device has a half mirror 1a, a fixed mirror 1b, and a movable mirror 1c. The emitted light (incident light) from near the pedestal is incident on the half mirror 1a. The light (first light) reflected by the half mirror 1a is reflected by the fixed mirror 1b and again enters the half mirror 1a. The light (second light) transmitted through the half mirror 1a is reflected by the movable mirror 1c and again enters the half mirror 1a. The light of the reflected light (first light) from the fixed mirror 1b that is transmitted through the half mirror 1a, and the light of the reflected light (second light) from the movable mirror 1c that is reflected by the half mirror 1a are mutually superimposed and output on the same optical path. By moving the movable mirror 1c back and forth, a phase difference is given between the first light and the second light.

As another example of the Fourier transform type spectroscopic device, there is also one in which the wave front of incident light is split, and an arbitrary phase difference is given to light on one side and then multiplexed again.

The dispersive spectroscope device disperses incident light according to the wavelength, and sequentially emits light separated for each wavelength. Examples of the dispersive spectroscope device include a prism type spectroscope and a diffraction grating type spectroscope. As an example, a configuration of a diffraction grating type spectroscope will be described.

The diffraction grating type spectroscope has an entrance slit, an exit slit, first and second spherical mirrors, and a diffraction grating. The entrance slit is positioned at the focal point of the first spherical mirror and the exit slit is positioned at the focal point of the second spherical mirror. Light that has entered from the entrance slit is emitted to the diffraction grating via the first spherical mirror. The first spherical mirror converts the incident light from the entrance slit into parallel light. The parallel light diffracted by the diffraction grating at an angle dependent on the wavelength is imaged on the exit slit via the second spherical mirror. By rotating the diffraction grating, the wavelength of the light emitted from the exit slit changes.

The image acquisition device 105 is a device capable of acquiring two-dimensional image information. For example, a CCD (charge coupled device) image sensor, a CMOS (complementary metal-oxide semiconductor) image sensor, an InGaAs (indium gallium arsenide) image sensor, a CIGS (copper indium gallium selenide) image sensor, or the like may be used as the image acquisition device 105. The light output from the spectroscopic device 104 is imaged on the light receiving plane of the image acquisition device 105. The image acquisition device 105 outputs two-dimensional image information obtained by converting the light output from the spectroscopic device 104 into brightness information indicating brightness and darkness of color according to its intensity. The two-dimensional image information output from the image acquisition device 105 is supplied to the calculation device 106.

The calculation device 106 controls the lighting operation of the light emission devices 101, 102 and the spectroscopic operation of the spectroscopic device 104, acquires image information from the image acquisition device 105, and performs image processing and living body authenticity determination processing. The calculation device 106 can be configured using, for example, a computer device or the like that operates according to a program.

In the case where the spectroscopic device 104 is a dispersive spectroscope device, the calculation device 106 causes the spectroscopic device 104 to perform a spectroscopic operation in which incident light is dispersed according to the wavelength, and light separated for each wavelength is sequentially emitted. For example, in the case where the spectroscopic device 104 is a diffraction grating type spectroscope, the calculation device 106 controls the rotation operation of the diffraction grating to thereby cause the diffraction grating type spectroscope to sequentially emit the light separated for each wavelength.

In the case where the spectroscopic device 104 is a Fourier transform type spectroscopic device, the calculation device 106 causes the spectroscopic device 104 to perform a spectroscopic operation in which a spatial phase difference is given to light that enters thereinto and an interference wave (interferogram) is emitted. For example, in the case where the spectroscopic device 104 is the Fourier transform type spectroscopic device shown in FIG. 2, the calculation device 106 moves the movable mirror 1c in a stepwise or continuous manner to thereby cause the Fourier transform type spectroscopic device to emit an interference wave (interferogram).

The positions of the spectroscopic device 104 and the imaging device 105 are not limited to the positions shown in the figure. The positions of the spectroscopic device 104 and the imaging device 105 may be not in the direction perpendicular to the pedestal of the measurement target placement device 103, but in a tilted direction.

Figure 3:
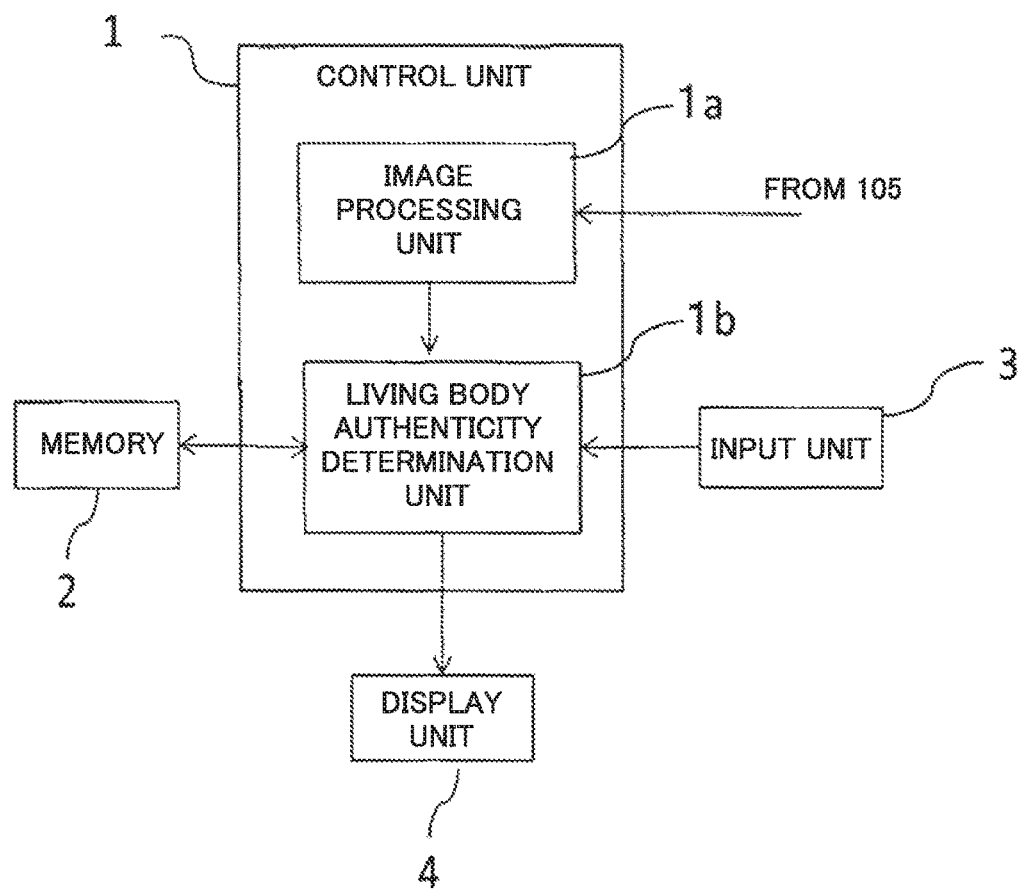
FIG. 3 is a block diagram showing a configuration of a calculation device used in the living body determination device shown in FIG. 1.

FIG. 3 shows the configuration of the calculation device 106. Referring to FIG. 3, the calculation device 106 has a control unit 1, a memory 2, an input unit 3, and a display unit 4.

The memory 2 is a storage device such as an HDD (hard disk drive) or a semiconductor memory, and stores a living body authenticity determination program and data necessary for performing image processing and living body authenticity determination processing. The living body determination program is a program for causing a computer (such as a CPU (Central Processing Unit)) to execute image processing and living body authenticity determination processing. The living body determination program may be supplied via a communication network (for example, the Internet), or may be supplied by a computer readable recording medium. The computer readable recording medium is, for example, an optical disc such as a CD (Compact Disc) or a DVD (Digital Versatile Disc), a USB (Universal Serial Bus) memory, a memory card, or the like.

The display unit 4 is a display device such as a liquid crystal display. The input unit 3 is a keyboard or the like. As the input unit 3, a touch panel provided on the display screen of the display unit 4 may be used.

The control unit 1 is composed of a CPU that operates according to a program, and it receives an operation instruction from the input unit 3 to thereby control the lighting operation of the light emission devices 101, 102 and the spectroscopic operation of the spectroscopic device 104, and execute the image processing and the living body authenticity determination processing. The control unit 1 has an image processing unit 1a and a living body authenticity determination unit 1b.

Figure 4A:
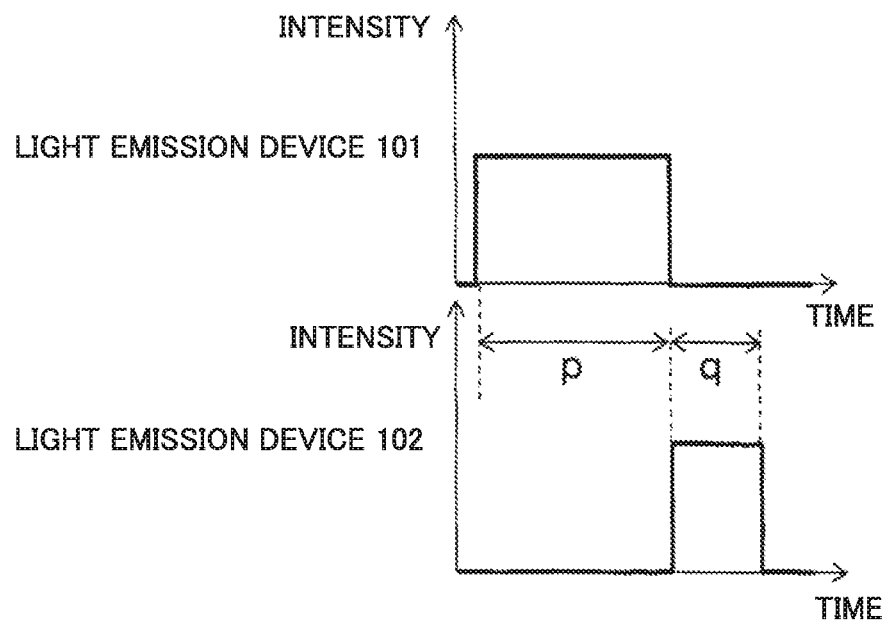
FIG. 4A is a diagram showing an example of lighting timing of a light emission device of the living body determination device shown in FIG. 1.

FIG. 4A shows an example of the lighting operation of the light emission devices 101, 102. In the period p, the image processing unit 1a turns on the light emission device 101 and turns off the light emission device 102, and in the period q, it turns off the light emission device 101 and turns on the light emission device 102. The periods p and q can be set appropriately.

In the period p, in a first light emission state where the light emission device 101 is turned on and the light emission device 102 is turned off, the image processing unit 1a controls the spectroscopic operation of the spectroscopic device 104 and acquires a plurality of pieces of image information I1 related to the measurement target 10a from the image acquisition device 105. Here, the plurality of pieces of image information I1 are image information for each wavelength of the light of the light 101a emitted by the light emission device 101 and transmitted through the measurement object 10a. In other words, the plurality of pieces of image information I1 are image information acquired for each spectrum of each spectrum of the light 101a.

The number of the pieces of image information I1 is determined by the wavelength resolution of the spectroscopic device 104. For example, in the case where the wavelength range of the light emission device 101 is 500 nm to 800 nm and the wavelength resolution of the spectroscopic device 104 is 5 nm, 61 pieces of two-dimensional image information are acquired as image information I1 from 500 nm to 800 nm in steps of 5 nm.

The image processing unit 1a calculates spectroscopic image information A by acquiring the spectroscopic information in a predetermined region of the image, from the plurality of image information I1. Here, the spectroscopic information indicates the wavelength dependence of the intensity in a predetermined region of the image. The predetermined region is the entire region of the measurement target 10a in the image or an arbitrary portion (specific pixel range) of the measurement target 10a and can be set preliminarily.

As an example, in FIG. 5 there is shown a relationship between image information and spectroscopic information. The subfigure (a) of FIG. 5 is total image information that combines the plurality of image information I1 into one. Here, the image of the finger is schematically shown, but this is an image created for the description, which is different from the actual image. The subfigure (b) of FIG. 5 is a graph showing the wavelength dependence of the intensity in each of the regions a1 to a4 of the total image information of the finger shown in the subfigure (a) of FIG. 5. The image processing unit 1a acquires spectroscopic information of a predetermined region of the total image information. For example, when the predetermined region is the region a1, the image processing unit 1a acquires the spectroscopic information based on the graph of the region a1 shown in the subfigure (b) of FIG. 5. Then, the image processing unit 1a calculates the spectroscopic image information A obtained by adding each image information I1 to the spectroscopic information. Note that the predetermined region may include a plurality of regions, and in that case, the spectroscopic image information A includes spectroscopic information of a plurality of portions.

In the period q, in a second light emission state where the light emission device 101 is turned off and the light emission device 102 is turned on, the image processing unit 1a controls the spectroscopic operation of the spectroscopic device 104 and acquires a plurality of pieces of image information I2 related to the measurement target 10a from the image acquisition device 105. Here, the plurality of pieces of image information I2 are image information for each wavelength of the light of the light 102a emitted by the light emission device 102 and reflected near the surface of the measurement target 10a. In other words, the plurality of pieces of image information I2 are image information acquired for each spectrum of each spectrum of the light 102a.

The number of the pieces of image information I2 is also determined by the wavelength resolution of the spectroscopic device 104. For example, in the case where the wavelength range of the light emission device 102 is 500 nm to 800 nm and the wavelength resolution of the spectroscopic device 104 is 5 nm, 61 pieces of two-dimensional image information are acquired as image information I2 from 500 nm to 800 nm in steps of 5 nm.

The image processing unit 1a acquires spectroscopic information from the plurality of pieces of image information I2 and calculates spectroscopic image information A obtained by adding each image information I2 to the spectroscopic information. Here, the spectroscopic information indicates the wavelength dependence of the intensity in a predetermined region of the image and has a relationship between image information and spectroscopic information such as the one shown in FIG. 5. The predetermined region is the entire region of the measurement target 10a in the image or an arbitrary portion (specific pixel range) of the measurement target 10a and can be set preliminarily. The predetermined region for acquiring the spectroscopic information in the image information I2 may be the same as or different from the predetermined region for acquiring the spectroscopic information in the image information I1.

The acquisition operation of the image information I1 and I2 is different between the case where the spectroscopic device 104 is a dispersive spectroscope device and the case where the spectroscopic device 104 is a Fourier transform type spectroscopic device.

In the case where the spectroscopic device 104 is a dispersive spectroscope device, light separated for each wavelength from the spectroscopic device 104 is sequentially supplied to the image acquisition device 105. Therefore the image acquisition device 105 outputs image information for each wavelength. In this case, the image processing unit 1a acquires the image information of each wavelength from the image acquisition device 105 for each of the image information I1 and I2.

On the other hand, in the case where the spectroscopic device 104 is a Fourier transform type spectroscopic device, an interference wave (interferogram) is supplied to the image acquisition device 105 from the spectroscopic device 104. Therefore the image acquisition device 105 outputs image information indicating the interferogram. In this case, the image processing unit 1a performs, for each of the image information I1, I2, Fourier transformation on the image information of the interferogram output from the image acquisition device 105 to thereby acquire image information for each wavelength.

Figure 4B:
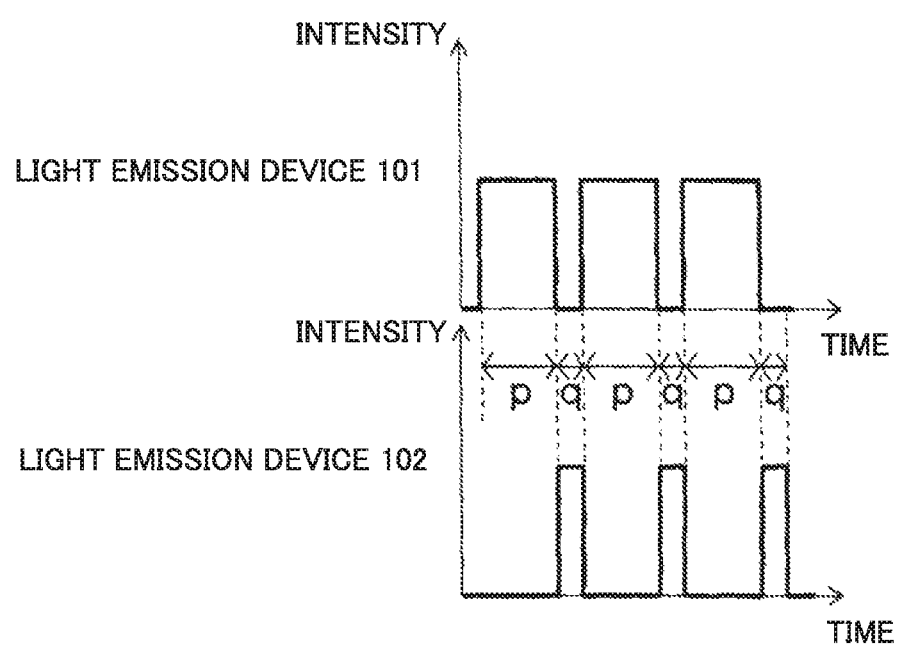
FIG. 4B is a diagram showing another example of lighting timing of the light emission device of the living body determination device shown in FIG. 1.

In the example shown in FIG. 4A, the light emission devices 101, 102 are switched once, but the present invention is not limited to this. For example, as shown in FIG. 4B, the light emission devices 101, 102 may be alternately switched a plurality of times. In this case, the image processing unit 1a calculates the spectroscopic image information A using the image information acquired in each p period, and calculates the spectroscopic image information B using the image information acquired in each q period.

The spectroscopic image information A, B calculated by the image processing unit 1a are supplied to the living body authenticity determination unit 1b. Based on the spectroscopic image information A, B, the living body authenticity determination unit 1b performs a living body authenticity determination as to whether or not the measurement target 10a is a living body.

Figure 6:
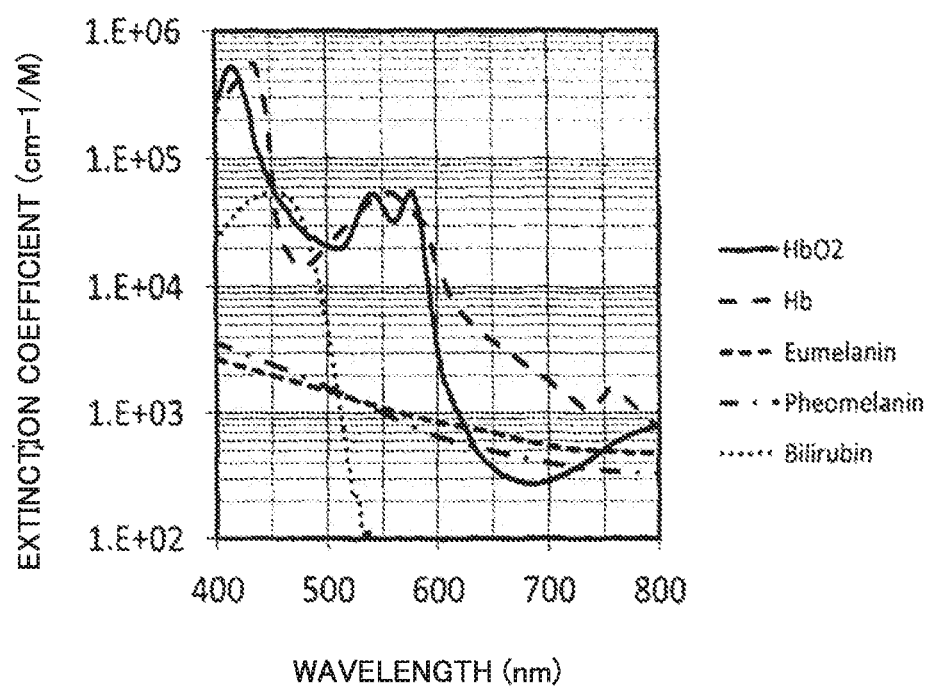
FIG. 6 is a characteristic diagram showing an example of a spectrum of a component related to a living body.

In the living body authenticity determination, the living body authenticity determination unit 1b compares spectra (spectral information) of spectroscopic image information A, B, respectively, with the spectra for living body determination stored in the memory 2. The spectra for living body determination is a combination of spectra related to living bodies. The spectra related to living bodies are spectra of components concerning a living body such as oxygenated hemoglobin (Oxyhemoglobin, HbO2), reduced hemoglobin (Deoxyhemoglobin, Hb), Bilirubin, Eumelanin, Pheomelanin, water, carotene, fat, and protein. As an example of living body related component spectra, FIG. 6 shows absorption spectra of oxygenated hemoglobin, reduced hemoglobin, Bilirubin, Eumelanin, and Pheomelanin. Here, these are the spectrum in the proximity of 36° C. in particular. The spectra related to a living body is not limited to the example shown in FIG. 6.

The combination of spectra related to a living body is, for example, a combination of absorption spectra (wavelength dependencies of extinction coefficients) of the biogenic components shown in FIG. 6. Combinations of spectra related to a living body (combinations of biogenic components) can be calculated, for example, based on the following Formula 1.

[Equation 1]

$$A(\lambda) = \log_{10} \sum_i (a_i x_i^{p_i})$$ (Formula 1)

Here, $\lambda$ is the wavelength, $a_i$ and $p_i$ are coefficients (fitting parameters), and $x_i$ is the wavelength dependence of the extinction coefficient of each biogenic component.

The living body authenticity determination unit 1b calculates a correlation degree between the spectra (spectral information) of each of the spectroscopic image information A, B and the spectra for living body determination, and determines whether or not the degree of correlation is not less than a predetermined value. If the degree of correlation is greater than or equal to the predetermined value, the living body authenticity determination unit 1b determines that the measurement target 10a is a living body, and displays on the display unit 4 that the living body authenticity determination is "true". If the degree of correlation is less than the predetermined value, the living body authenticity determination unit 1b determines that the measurement target 10a is not a living body, and displays on the display unit 4 that the living body authenticity determination is "false".

Next, the living body determination operation of the living body determination device 10 will be described in detail.

Figure 7:
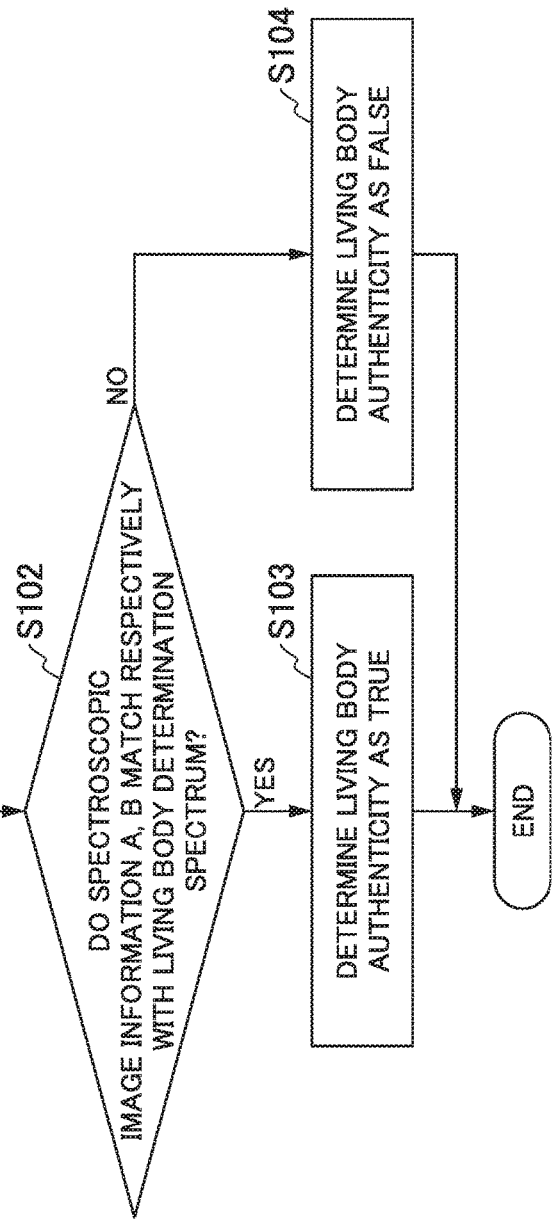
FIG. 7 is a flowchart showing a procedure of a living body determination operation of the living body determination device shown in FIG. 1.

FIG. 7 shows a procedure of the living body determination operation. Hereinafter, the living body determination operation will be described with reference to FIG. 1, FIG. 3, and FIG. 7. In this example, a white LED is used as the light emission device 101, a Fourier transform type spectroscopic device is used as the spectroscopic device 104, and a CMOS image sensor is used as the image acquisition device 105.

First, in Step S100, in the first light emission state where the light emission device 101 is turned on and the light emission device 102 is turned off, the image processing unit 1a controls the spectroscopic operation of the spectroscopic device 104 and acquires a plurality of pieces of image information I1 related to the measurement target 10a from the image acquisition device 105. Then, the image processing unit 1a acquires the spectroscopic information based on the total image information of the plurality of pieces of image information I1, and calculates spectroscopic image information A.

Figure 8:
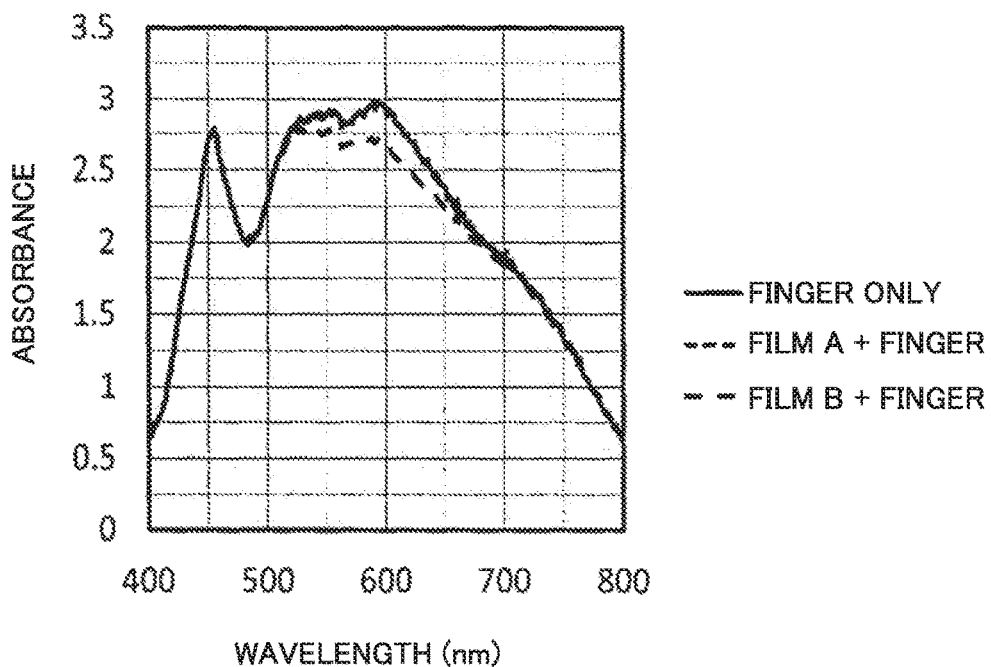
FIG. 8 is a characteristic diagram showing an example of a transmission spectrum that is a calculation result of spectroscopic image information.

FIG. 8 shows an example of a transmission spectrum that is a calculation result of the spectroscopic image information A. In FIG. 8, the horizontal axis represents wavelength and the vertical axis represents absorbance (normalized). There is shown an example of measurement of the transmission spectrum (absorbance) in each of the cases where the measurement target 10a is "finger only", "film A+finger", and "film B+finger". "Finger only" is indicated by a solid line. "Film A+finger" is a case where the film A is attached on a finger and is indicated by a dashed line with short intervals. "Film B+finger" is a case where the film B is attached on a finger and is indicated by a dashed line with long intervals. The transmission spectrum of the measurement target 10a is derived from the internal absorption spectrum of the measurement target 10a.

First, in Step S101, in the second light emission state where the light emission device 101 is turned off and the light emission device 102 is turned on, the image processing unit 1a controls the spectroscopic operation of the spectroscopic device 104 and acquires a plurality of pieces of image information I2 related to the measurement target 10a from the image acquisition device 105. Then, the image processing unit 1a acquires the spectroscopic information from the total image information of the plurality of pieces of image information I2, and calculates spectroscopic image information B.

Figure 9:
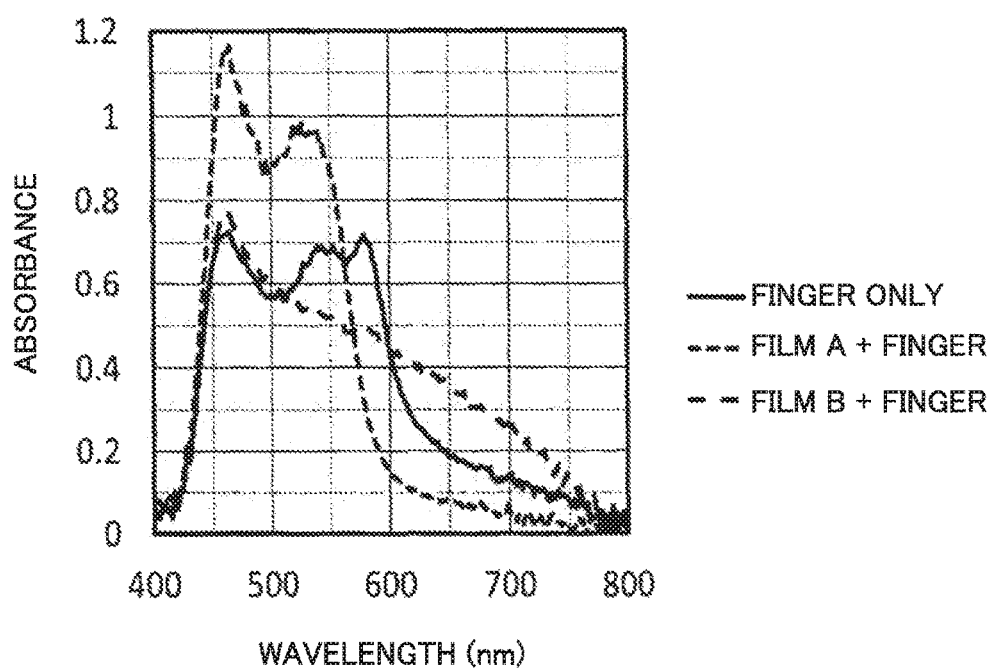
FIG. 9 is a characteristic diagram showing an example of a reflection spectrum that is a calculation result of spectroscopic image information.

FIG. 9 shows an example of a reflection spectrum that is a calculation result of the spectroscopic image information B. In FIG. 9, the horizontal axis represents wavelength and the vertical axis represents absorbance (normalized). There is shown an example of measurement of the reflection spectrum (absorbance) in each of the cases where the measurement target 10a is "finger only", "film A+finger", and "film B+finger". "Finger only" is indicated by a solid line. "Film A+finger" is a case where the film A is attached on a finger and is indicated by a dashed line with short intervals. "Film B+finger" is a case where the film B is attached on a finger and is indicated by a dashed line with long intervals. The reflection spectrum of the measurement target 10a is derived from the absorption spectrum in the vicinity of the surface of the measurement target 10a.

Next, in Step S102, the living body authenticity determination unit 1b determines whether or not the spectra of each of the spectroscopic image information A, B matches the spectrum for living body determination (biogenic component combination). Specifically, the living body authenticity determination unit 1b calculates a correlation degree between the spectrum of each of the spectroscopic image information A, B and the spectrum for living body determination, and determines whether or not the degree of correlation is not less than a predetermined value.

Figure 10:
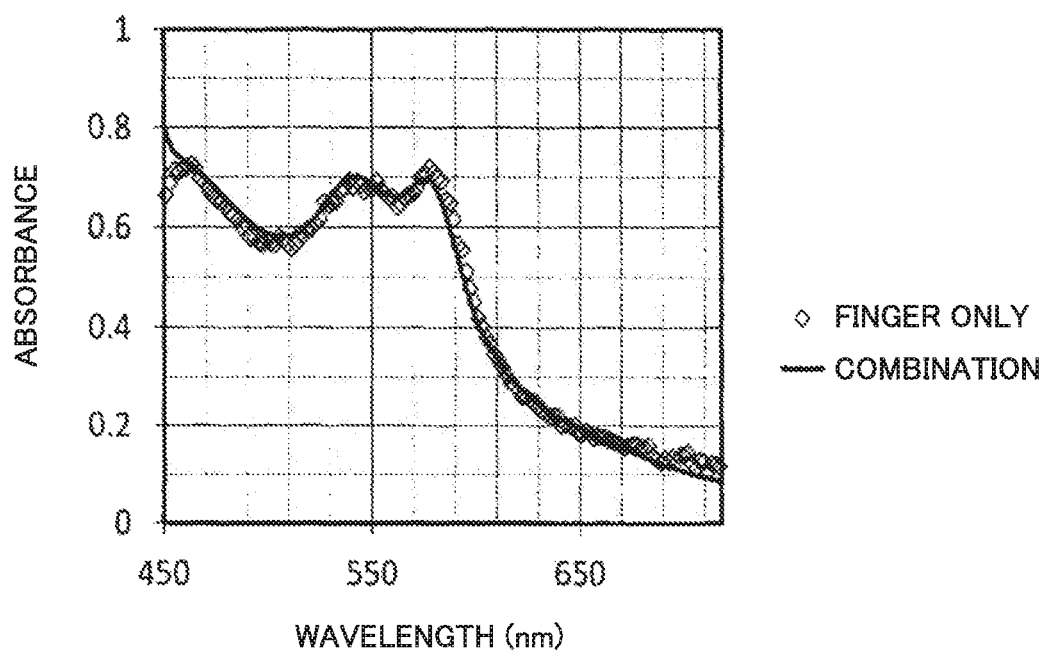
FIG. 10 is a characteristic diagram showing a relationship between a reflection spectrum in a case of a finger only and a spectrum for living body determination.

As an example, in FIG. 10 there is shown a relationship between a reflection spectrum of the spectroscopic image information B and a spectrum for living body determination in the case of "finger only". In FIG. 10, the horizontal axis represents wavelength and the vertical axis represents absorbance (normalized). "Finger only" is indicated by rhombus symbols. The spectrum for living body determination is indicated by a solid line. Here, the spectrum for living body determination is a combination of absorption spectra of biogenic components shown in FIG. 6 (wavelength dependencies of extinction coefficients), and it can be calculated based on Formula 1 described above.

Figure 11:
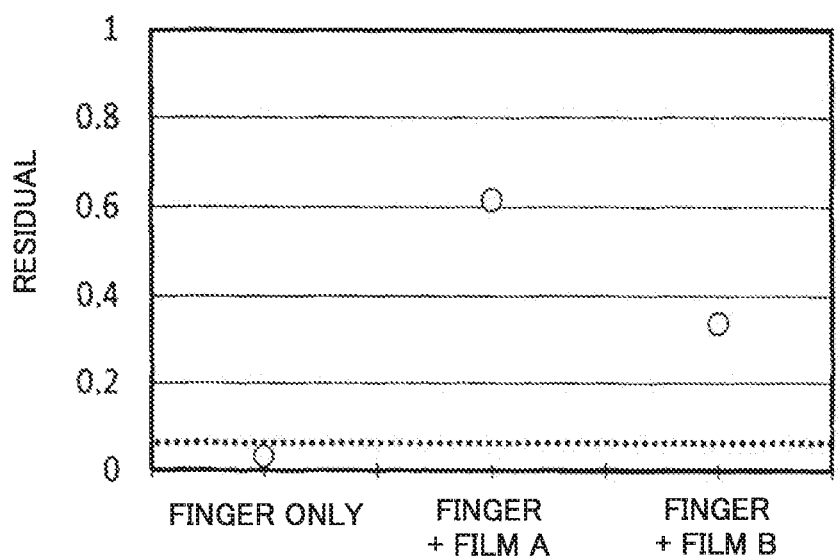
FIG. 11 is a diagram for explaining residuals between reflection spectrum of finger only, film A+finger, and film B+finger and living body determination spectrum.

In FIG. 11 there are shown residuals between reflection spectrum of finger only, film A+finger, and film B+finger, respectively and living body determination spectrum. Here, the residual is a mean square root of the difference between the reflection spectrum and the living body determination spectrum.

The residual between the reflection spectrum of "finger only" and the living body determination spectrum is not more than a threshold value (for example, 0.08). In this case, the living body authenticity determination unit 1b determines the correlation degree between the spectroscopic image information B and the spectrum for living body determination as being not less than a predetermined value.

On the other hand, the residual between the reflection spectrum of "finger+film A" and the living body determination spectrum exceeds the threshold value. In this case, the living body authenticity determination unit 1b determines the correlation degree between the spectroscopic image information B and the spectrum for living body determination as being less than the predetermined value. Similarly, since the residual between the reflection spectrum of "finger+film B" and the living body determination spectrum exceeds the threshold value, the living body authenticity determination unit 1b determines the correlation degree between the spectroscopic image information B and the spectrum for living body determination as being less than the predetermined value.

Also regarding the transmission spectrum, as with the reflection spectrum, it is possible to determine the level of the correlation degree from the residual between the transmission spectrum and the living body determination spectrum. In the case where the residual between the transmission spectrum and the living body determination spectrum is not more than the threshold value, the living body authenticity determination unit 1b determines the correlation degree between the spectroscopic image information A and the spectrum for living body determination as being not less than the predetermined value. On the other hand, in the case where the residual between the transmission spectrum and the living body determination spectrum exceeds the threshold value, the living body authenticity determination unit 1b determines the correlation degree between the spectroscopic image information A and the spectrum for living body determination as being less than the predetermined value.

In Step S102, if the degree of correlation is determined as being greater than or equal to the predetermined value, then in Step S103 the living body authenticity determination unit 1b determines that the measurement target 10a is a living body, and displays on the display unit 4 that the living body authenticity determination is "true".

In Step S102, if the degree of correlation is determined as being less than the predetermined value, then in Step S104 the living body authenticity determination unit 1b determines that the measurement target 10a is not a living body, and displays on the display unit 4 that the living body authenticity determination is "false".

Here, even if the correlation degree is equal to or greater than the predetermined value, when the combination of the living body determination spectrum and the biogenic component is abnormal, it is determined that the measurement target 10a is not a living body. That is to say, in the case where the correlation degree is equal to or greater than the predetermined value and the combination of the living body determination spectrum and the biogenic component is normal, it is determined that the measurement target 10a is a living body. The case where the combination of the living body determination spectrum and the biogenic component is abnormal means that the proportion of the reduced hemoglobin is extremely high with respect to the proportion of the oxygenated hemoglobin, or that the living body determination spectrum is lower than the predetermined value. In this case, the measurement target 10a is determined as not being a living body. The case where the proportion of reduced hemoglobin is extremely high with respect to the proportion of oxygenated hemoglobin is for example a case where the oxygen concentration in the blood becomes lower. This is a case, for example, where the degree of arterial blood oxygen saturation (SaO2) is lower than a predetermined value. The case where it is lower than the predetermined value is, for example, a case where SaO2<90%. The case where the spectrum for living body determination is lower than the predetermined value is, for example, the case where the absorbance at around 550 nm of the living body determination spectrum is 0.3 or less, or the absorbance at around 600 nm is 0.2 or less.

According to the living body determination device 10 of the present exemplary embodiment, since the spectroscopic image information A, B (reflection spectrum and transmission spectrum) are used, it is possible to determine whether or not it is a living body from the surface and the inside of the measurement target 10a. Therefore, as compared with the multifactor authentication system disclosed in Patent Document 3 that performs living body determination based on a diffuse reflection spectrum from a finger, it is possible to reliably detect a film-shaped forged fingerprint fragment and improve the precision of living body determination.

In addition, it is possible to calculate the spectroscopic image information A, B (reflection spectrum and transmission spectrum) related to an arbitrary portion of the measurement target 10a. Since it is difficult for a third party to forge spectroscopic image information of such an arbitrary portion, the level of difficulty in forging is improved as compared with the authentication device disclosed in Patent Document 2 or the image capturing device for forgery determination disclosed in Patent Document 4.

Moreover, since the light emission device 102, the spectroscopic device 104, and the image acquisition device 105 are used in combination with the living body determination device 10 and a biometric authentication device described later, it is possible to suppress an increase in size of the device. Furthermore, since no ultrasonic wave transmitting means and no ultrasonic wave receiving means are used, it is possible to accurately perform living body determination even in an environment where noise unique to ultrasonic waves is likely to occur. Therefore, compared to the biometric information measurement device disclosed in Patent Document 1, it is possible to suppress an increase in size of the device and improve the accuracy of living body determination.

In the living body determination device of the first exemplary embodiment described above, the light emission devices 101, 102 can be referred to respectively as first and second light emission means, the spectroscopic device 104 can be referred to as spectroscopic means, and the image acquisition device 105 can be referred to as image acquisition means. Each of the first and second light emission means may include a plurality of light emission devices.

First Application Example: Biometric Authentication Device

Next, a biometric authentication device to which the living body determination device of the first exemplary embodiment described above is applied will be described.

The biometric authentication device of the present example is such that the calculation device 106 of the living body determination device 10 shown in FIG. 1 is replaced with a calculation device 106*a* having a biometric authentication function. The configuration other than the calculation device 106*a* is basically the same as that of the living body determination device 10.

Figure 12:
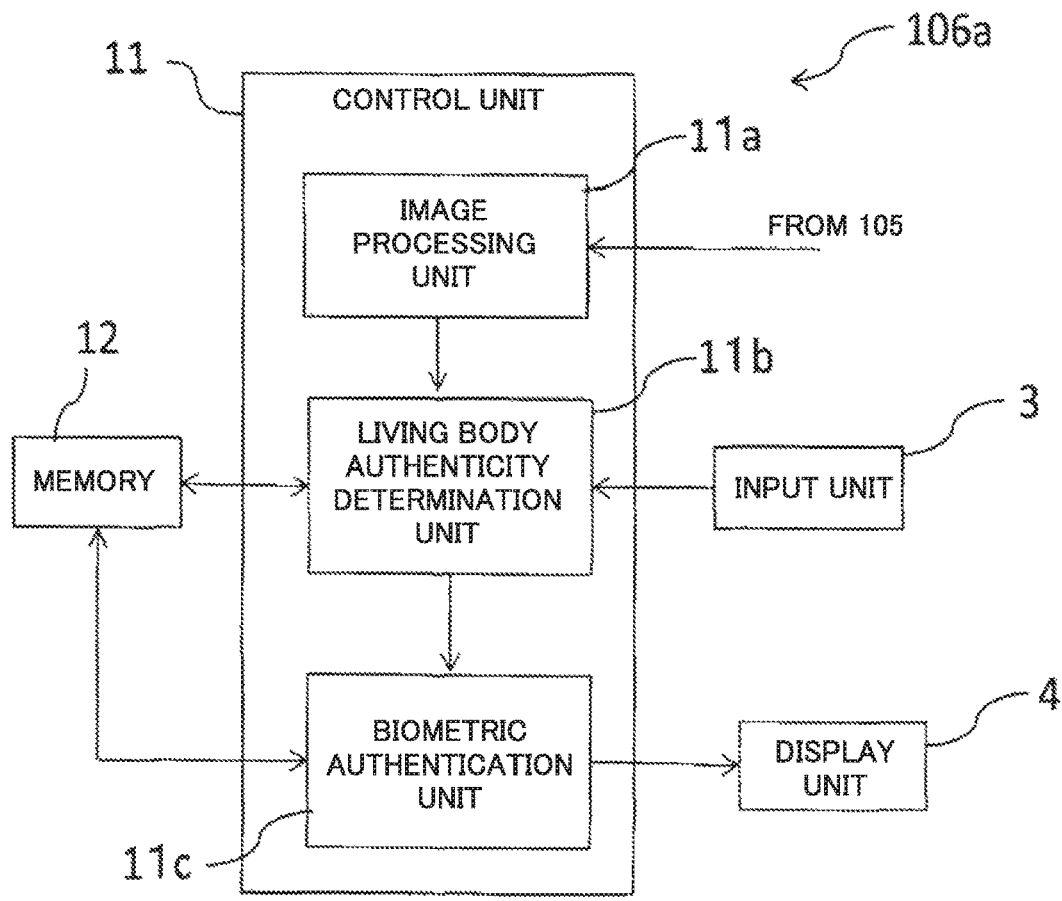
FIG. 12 is a block diagram showing a configuration of a calculation device of a biometric authentication device being a first application example to which the living body determination device of the first exemplary embodiment of the present invention is applied.

FIG. 12 is a block diagram showing the configuration of the calculation device 106*a*.

Referring to FIG. 12, the calculation device 106*a* has a control unit 11, a memory 12, an input unit 13, and a display unit 14. The input unit 13 and the display unit 14 are the same as the input unit 3 and the display unit 4 shown in FIG. 3.

The memory 12 is similar to the memory 2 shown in FIG. 3, and stores a program and data (including a biometric authentication database) necessary for performing biometric authentication. This biometric authentication program can also be provided by a communication network (for example, the Internet) or a computer readable recording medium (an optical disc such as a CD or a DVD, a USB memory, a memory card, or the like).

The control unit 11 is composed of a CPU that operates according to a program, and it receives an operation instruction from the input unit 13 to thereby control the lighting operation of the light emission devices 101, 102 and the spectroscopic operation of the spectroscopic device 104, and execute the image processing, the living body authenticity determination processing, and the biometric authentication processing. The control unit 11 has an image processing unit 11*a*, a living body authenticity determination unit 11*b*, and a biometric authentication unit 11*c*.

The living body authenticity determination unit 11*b* is the same as the living body authenticity determination unit 1*b* shown in FIG. 3. In addition to the function of the image processing unit 1*a* shown in FIG. 3, the image processing unit 11*a* has a function of acquiring biometric information D that indicates physical features. The measurement target 10*a* is a portion (such as a finger) that indicates a physical feature.

The image processing unit 11*a* controls the lighting operation of the light emission devices 101, 102 as shown in FIG. 4A or FIG. 4B. In the period p in the first light emission state where the light emission device 101 is turned on and the light emission device 102 is turned off, the image processing unit 11*a* acquires a plurality of pieces of image information I1 related to the measurement target 10*a* from the image acquisition device 105. Then, the image processing unit 11*a* calculates the spectroscopic image information A using the plurality of pieces of image information I1. The calculation operation of the spectroscopic image information A is basically the same as the calculation operation of the spectroscopic image information A of the image processing unit 1*a* shown in FIG. 3. However, while predetermined regions of the image can be set preliminarily, they are limited to portions that indicate physical features (the regions a1, a2 shown in FIG. 5).

In the period q in the second light emission state where the light emission device 101 is turned off and the light emission device 102 is turned on, the image processing unit 11*a* acquires a plurality of pieces of image information I2 related to the measurement target 10*a* from the image acquisition device 105. Then, the image processing unit 11*a* calculates the spectroscopic image information B and biometric information D using the plurality of pieces of image information I2. The calculation operation of the spectroscopic image information B is the same as the calculation operation of the spectroscopic image information B of the image processing unit 1*a* shown in FIG. 3. However, predetermined regions on the image are limited to portions that indicate physical features such as the regions a1, a2 shown in FIG. 5.

Figure 13:
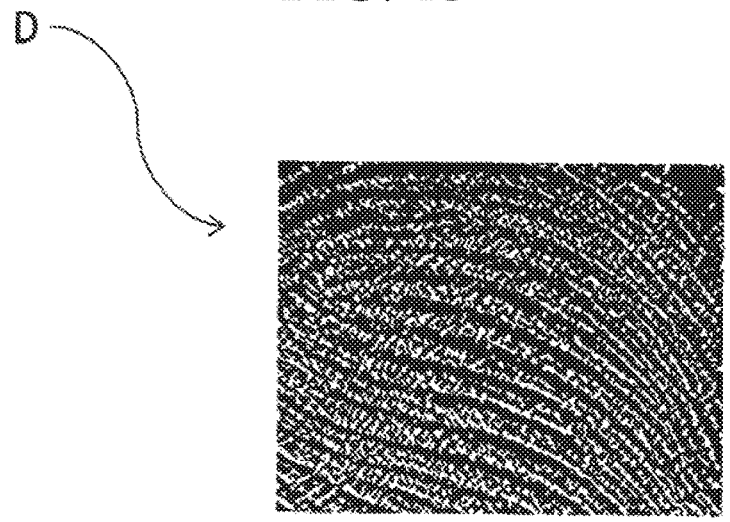
FIG. 13 is a schematic diagram showing an example of a fingerprint, which is biometric information.

The image processing unit 11*a* calculates biometric information D related to depressions and protrusions on the surface of the measurement target 10*a*, based on the image information obtained by integrating (averaging) the plurality of pieces of image information I2. For example, in the case where the measurement target 10*a* is a finger, the image processing unit 11*a* calculates biometric information D that indicates depression and protrusion information (fingerprint) of the pad of the finger from the averaged image information. FIG. 13 shows an example of a fingerprint calculated as biometric information D. The number of pieces of the image information I2 used for calculating biometric information D is not particularly limited. The image processing unit 11*a* can calculate the biometric information D using two or more of the plurality of pieces of image information I2 acquired by the image processing unit 11*a*.

When the living body authenticity determination unit 1*b* determines that the measurement target 10*a* is a living body, the biometric authentication unit 11*c* acquires information (biometric authentication information) required for biometric authentication from the memory 12, and compares this biometric authentication information with the biometric information D. For example, when biometric authentication is performed using a fingerprint, fingerprint information of a user is preliminarily stored in the memory 12 as biometric authentication information. The biometric authentication unit 11*c* acquires the fingerprint information from the memory 12 and compares the fingerprint information with the biometric information D.

If the biometric information D matches with the biometric authentication information, the biometric authentication unit 11*c* determines that the user is an authorized user, and displays on the display unit 4 information indicating that the authentication has been successful.

If the biometric information D does not match with the biometric authentication information, the biometric authentication unit 11*c* determines that the user is an unauthorized user, and displays on the display unit 4 information indicating an authentication error. Also in a case where the living body authenticity determination unit 1b determines the measurement target 10a as not being a living body, the biometric authentication unit 11c displays on the display unit 4 information indicating an authentication error.

Next, a biometric authentication operation of the biometric authentication device 10 of the present example will be described in detail.

Figure 14:
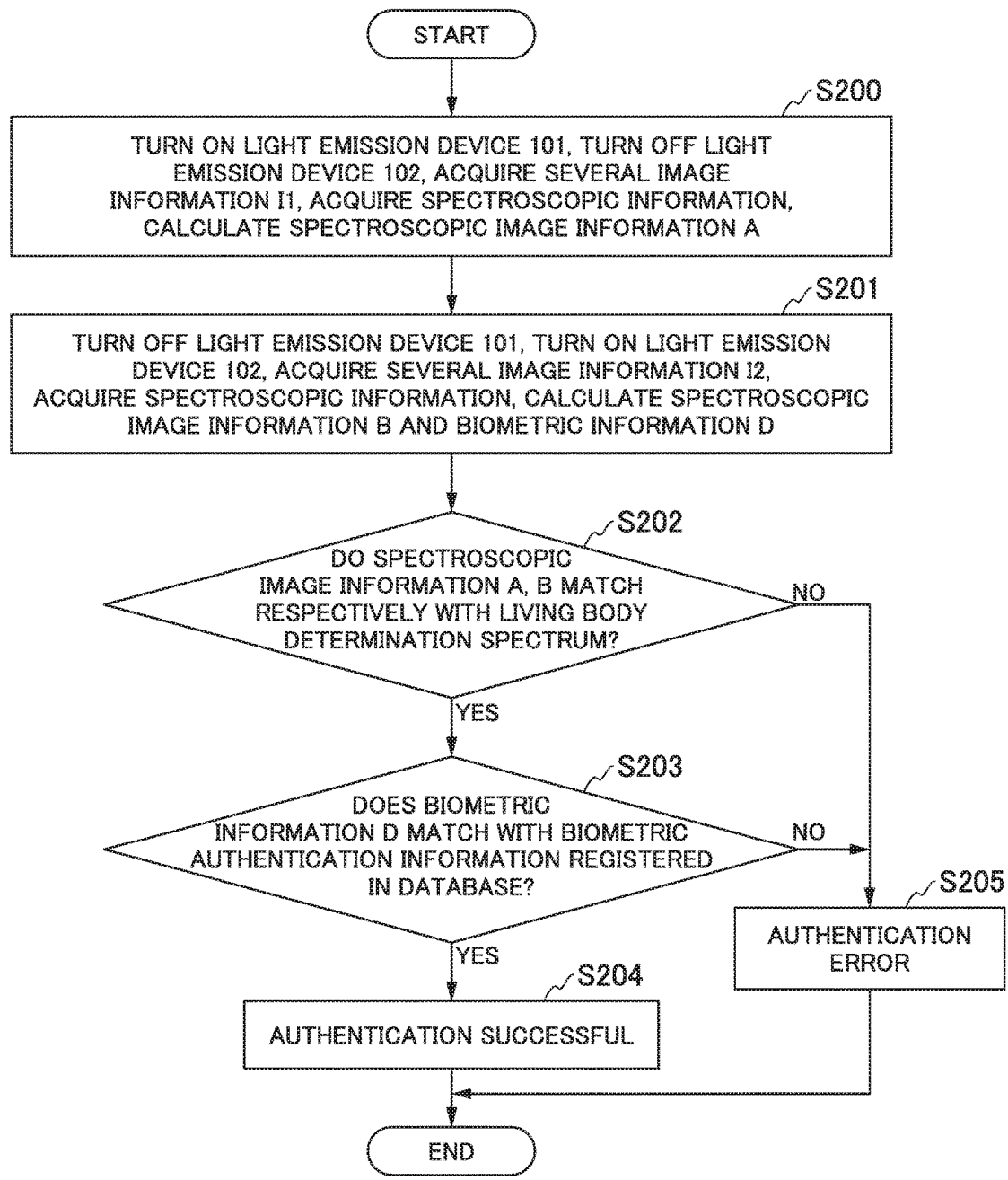
FIG. 14 is a flowchart showing a procedure of a biometric authentication operation of the biometric authentication device of the first application example.

FIG. 14 shows a procedure of the biometric authentication operation. Hereunder, the biometric authentication operation will be described with reference to FIG. 12 and FIG. 14. In this example, a white LED is used as the light emission device 101, a Fourier transform type spectroscopic device is used as the spectroscopic device 104, and a CMOS image sensor is used as the image acquisition device 105.

First, in Step S200, in the first light emission state where the light emission device 101 is turned on and the light emission device 102 is turned off, the image processing unit 11a controls the spectroscopic operation of the spectroscopic device 104 and acquires a plurality of pieces of image information I1 related to the measurement target 10a from the image acquisition device 105. Then, the image processing unit 11a acquires the spectroscopic information from the total image information of the plurality of pieces of image information I1, and calculates spectroscopic image information A.

In Step S201, in the second light emission state where the light emission device 101 is turned off and the light emission device 102 is turned on, the image processing unit 11a controls the spectroscopic operation of the spectroscopic device 104 and acquires a plurality of pieces of image information I2 related to the measurement target 10a from the image acquisition device 105. Then, the image processing unit 11a acquires the spectroscopic information from the total image information of the plurality of pieces of image information I2 and calculates spectroscopic image information B, and also calculates the biometric information D from the plurality of pieces of image information I2.

In Step S202, the living body authenticity determination unit 11b determines whether or not the spectra of each of the spectroscopic image information A, B matches the spectrum for living body determination. Specifically, the living body authenticity determination unit 11b calculates a correlation degree between the spectrum of each of the spectroscopic image information A, B and the spectrum for living body determination, and determines whether or not the degree of correlation is not less than a predetermined value.

If determined as "Yes" in Step S202, then in Step S203, the biometric authentication unit 11c acquires the biometric authentication information from the memory 12 and determines whether or not the biometric information D matches with the biometric authentication information. If the biometric information D matches with the biometric authentication information, then in Step S204, the biometric authentication unit 11c determines the user as being an authorized user, and displays on the display unit 4 information indicating that the authentication has been successful.

If determined as "No" in Step S202 or in Step S203, then in Step S205, the biometric authentication unit 11c determines the user as being an unauthorized user, and displays on the display unit 4 information indicating an authentication error.

According to the biometric authentication device of the present example, since biometric authentication is performed on a portion that has been determined as a living body by means of highly accurate living body determination, which makes forgery difficult, reliability of biometric authentication can be improved while ensuring a high level of security.

Moreover, since the light emission device 102, the spectroscopic device 104, and the image acquisition device 105 are used in combination with the living body determination device 10 and the biometric authentication device of the present example, it is possible to suppress an increase in size of the device.

Note that the biometric authentication information may be stored in an external storage device (database) or in a database server. In this case, the biometric authentication unit 11c is connected to the external storage device (database) or the database server via a network (not shown in the figure).

Also, biometric authentication information is registered in the database, but it is not limited to this. The biometric authentication information may be stored in a storage means such as an IC (Integrated Circuit) tag. For example, if an IC tag storing biometric authentication information is mounted on a passport or the like, the biometric authentication information is read from the IC tag when the passport is presented, and the biometric authentication information and biometric information D are compared with each other.

Further, the image processing unit 11a may select, from the plurality of pieces of image information I2, image information of the wavelength band that makes acquisition of the biological information D (surface depression and protrusion information) easy. For example, the image processing unit 11a may, from the plurality of pieces of image information I2, remove image information on the longer wavelength side and select image information on the shorter wavelength side.

Hereinafter, a method of selecting the image information I2 will be described in detail.

The wavelength range of the light emission device 102 is a wavelength range from the visible light range to the near-infrared light range (approximately 380 nm to 2500 nm). Diffusion occurs in all wavelength ranges, but wavelength dependence of absorbance (extinction coefficient, transmittance) is great.

Since the absorbance is relatively great in the blue to green wavelength range (approximately 400 to 600 nm), the light diffused on the surface of the measurement target 10a is detected by the image acquisition device 105 via the spectroscopic device 104. Therefore, with respect to the wavelength range of blue to green (approximately 400 to 600 nm), it is possible to easily and highly accurately acquire the biometric information D from the image information I2.

On the other hand, since the absorbance is relatively small in the red to near-infrared wavelength range (approximately 600 to 900 nm), light penetrates into the measurement target 10a. As a result, not only the light diffused on the surface of the measurement target 10a but also the light diffused inside the measurement target 10a is detected by the image acquisition device 105 via the spectroscopic device 104. Therefore, with respect to the wavelength range of red to near-infrared (approximately 600 to 900 nm), it is possible to easily and highly accurately acquire the biometric information D from the image information I2.

Figure 15:
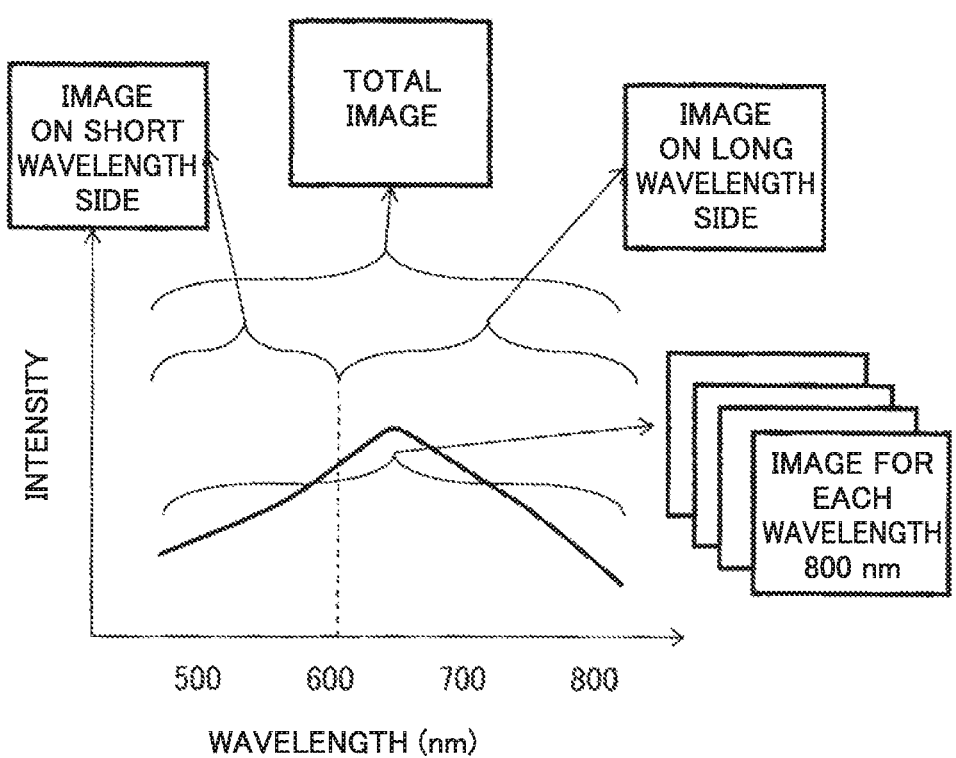
FIG. 15 is a diagram for explaining an example of image information of wavelength range 500 to 800 nm.

FIG. 15 shows an example of the image information I2 in the wavelength range (500 to 800 nm). As shown in FIG. 15, of the spectroscopic information of the predetermined region of the total image information, the side of the wavelength longer than red (for example, 600 nm or more) may be removed, and only the side of the wavelength shorter than red (for example, less than 600 nm) used. As a result, it is possible to eliminate the influence of diffused light inside the living body at the red to near-infrared region wavelength, in which the level of absorbance is low. Therefore, the biometric information D can be easily and highly accurately acquired. As a removal method, there are a method of obtaining a plurality of pieces of image information only on the side of the wavelength shorter than red by integrating them, and a method of arranging a wavelength selection filter between the image acquisition device 105 and the spectroscopic device 104.

Further, in the living body determination device 10 or the biometric authentication device of the present example, an information output means such as a speaker may be used instead of the display unit 4. In the case of using a speaker, information indicating whether or not it is a living body, and information indicating authentication success and authentication error are reported by means of sound.

Second Exemplary Embodiment

A living body determination device according to a second exemplary embodiment of the present invention has a configuration similar to that of the first exemplary embodiment. However, it differs from the first exemplary embodiment in that it uses brightness change information C indicating temporal changes in brightness in addition to spectroscopic image information A, B. Here, the configuration that differs from that of the first exemplary embodiment will be mainly described, and a description of the same configuration will be omitted.

In the period p shown in FIG. 4A or FIG. 4B, the image processing unit 1a turns on the light emission device 101 and turns off the light emission device 102. The image processing unit 1a acquires a plurality of pieces of image information I1 related to the measurement target 10a from the image acquisition device 105, and calculates the spectroscopic image information A and brightness change information C.

In the period q shown in FIG. 4A or FIG. 4B, the image processing unit 1a turns off the light emission device 101 and turns on the light emission device 102. The image processing unit 1a acquires a plurality of pieces of image information I2 related to the measurement target 10a from the image acquisition device 105, and calculates the spectroscopic image information B.

The method of calculating the spectroscopic image information A, B is as described in the first exemplary embodiment. The brightness change information C is derived from the pulse wave of the measurement target 10a. The calculation operation of the brightness change information C is different between the case where the spectroscopic device 104 is a dispersive spectroscope device and the case where the spectroscopic device 104 is a Fourier transform type spectroscopic device.

When the spectroscopic device 104 is a dispersive spectroscope device having a wavelength resolution of 5 nm and the wavelength range of the light emission device 101 is 500 nm to 800 nm, the image processing unit 1a acquires 61 pieces of image information I1 from 500 nm to 800 nm in steps of 5 nm in 5 seconds for example. The image processing unit 1a performs numerical processing on the 61 pieces of image information I1 to calculate brightness change information C that indicates the temporal changes in brightness (temporal changes in pulse wave) in a predetermined region of the image. The predetermined region is the entire region of the measurement target 10a or an arbitrary portion of the measurement target 10a in the image (a specific pixel range or specific pixels). In the case where the predetermined region is the entire region or a specific pixel range, the average value of the brightness of each pixel is used.

Note that the image processing unit 1a may acquire image information separately from the image information I1 to thereby calculate the brightness change information C. For example, when the frame rate of the image acquisition device 105 is 30 fps, the image processing unit 1a may capture 90 pieces of image information in 3 seconds for a specific wavelength (for example, 700 nm), and calculate the brightness change information C based on these pieces of image information. In this case, the 61 pieces of image information I1 for calculating the spectroscopic image information A and the 90 pieces of image information for calculating the brightness change information C are used.

On the other hand, in the case where the spectroscopic device 104 is a Fourier transform type spectroscopic device, the image acquisition device 105 outputs image information indicating the interferogram. In this case, the image processing unit 1a calculates the brightness change information C based on the image information of the interferogram output from the image acquisition device 105.

For example, when the frame rate of the image acquisition device 105 is 60 fps, the image processing unit 1a captures 300 pieces of image information of the interferogram in 5 seconds, and calculates the brightness change information C by performing pulse wave emphasis processing on these pieces of image information. Here, the pulse wave emphasis processing includes image processing to which a digital filter is applied and inter-pixel averaging processing.

Note that the image processing unit 1a performs, for each of the image information I1, I2, Fourier transformation on the image information of the interferogram output from the image acquisition device 105 to thereby acquire image information for each wavelength. At this time, it is preferable that Fourier transform be performed after removing pulse waves from the interferogram.

Next, a living body determination operation of the living body determination device of the present exemplary embodiment will be described specifically.

Figure 16:
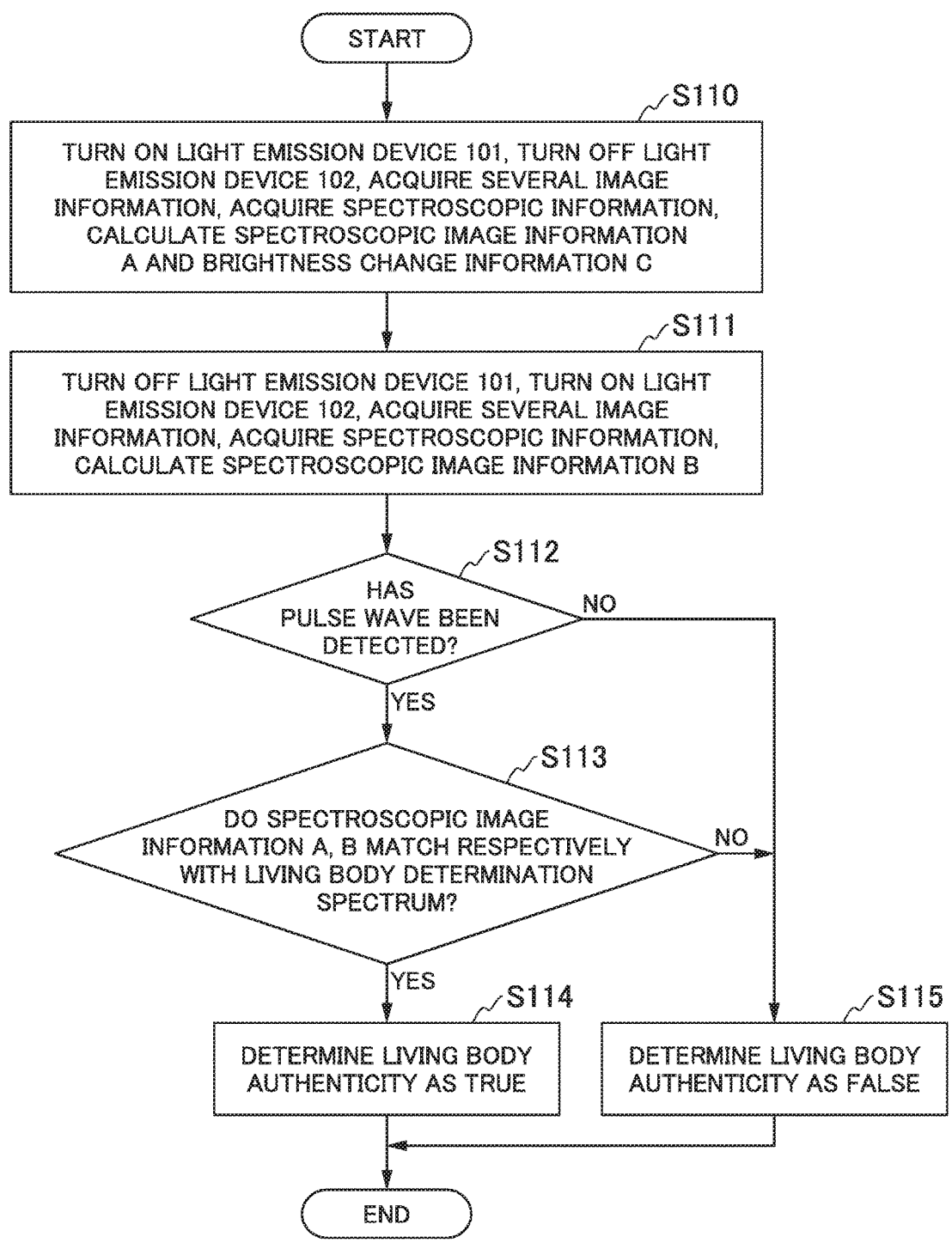
FIG. 16 is a flowchart showing a procedure of a living body determination operation of a living body determination device of a second exemplary embodiment of the present invention.

FIG. 16 shows a procedure of the living body determination operation. In this example, a white LED is used as the light emission device 101, a Fourier transform type spectroscopic device is used as the spectroscopic device 104, and a CMOS image sensor is used as the image acquisition device 105.

First, in Step S110, in the first light emission state where the light emission device 101 is turned on and the light emission device 102 is turned off, the image processing unit 1a controls the spectroscopic operation of the spectroscopic device 104 and acquires a plurality of pieces of image information related to the measurement target 10a from the image acquisition device 105. Then, the image processing unit 1a acquires spectroscopic information from the total image information of the plurality of pieces of acquired image information and calculates spectroscopic image information A, and also calculates brightness change information C from the plurality of pieces of acquired image information. For example, a spectrum of the spectroscopic image information A as shown in FIG. 8 is obtained.

Figure 17:
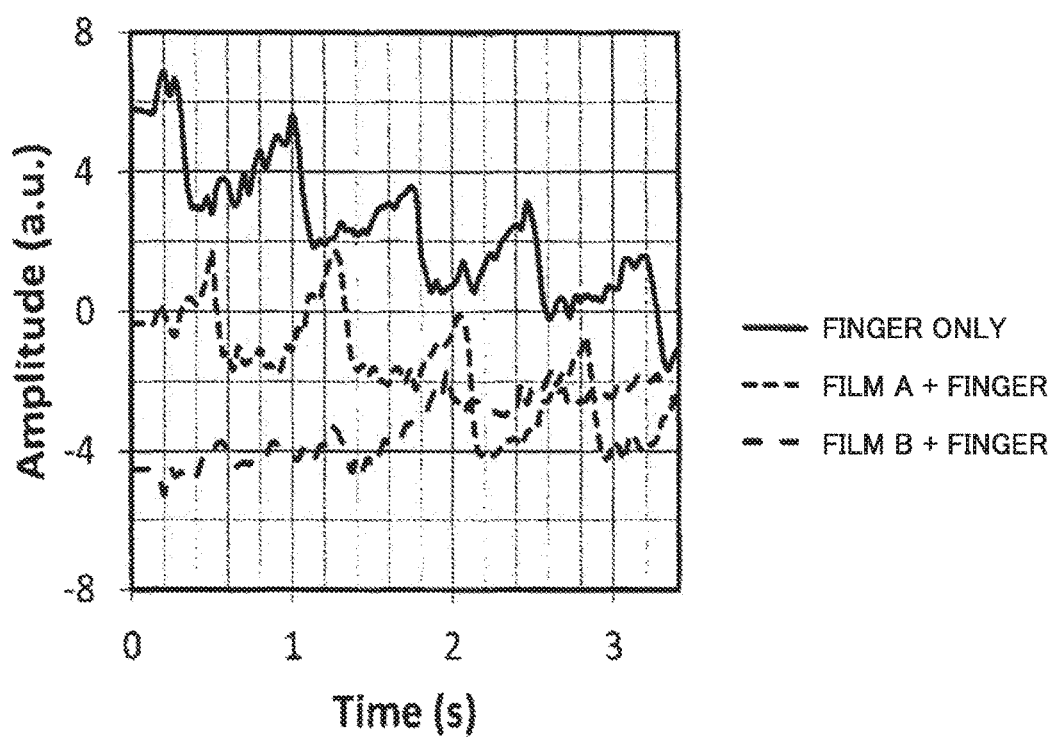
FIG. 17 is a characteristic diagram showing an example of a calculation result of brightness change information.

The brightness change information C is derived from the pulse wave of the measurement target 10a. FIG. 17 shows a calculation result of the brightness change information C. In FIG. 17, the horizontal axis represents time (seconds) and the vertical axis represents amplitude. There is shown a measurement example in each of the cases where the measurement target 10a is "finger only", "film A+finger", and "film B+finger". "Finger only" is indicated by a solid line. "Film A+finger" is a case where the film A is attached on a finger and is indicated by a dashed line with short intervals. "Film B+finger" is a case where the film B is attached on a finger and is indicated by a dashed line with long intervals.

First, in Step S111, in the second light emission state where the light emission device 101 is turned off and the light emission device 102 is turned on, the image processing unit 1a controls the spectroscopic operation of the spectroscopic device 104 and acquires a plurality of pieces of image information I2 related to the measurement target 10a from the image acquisition device 105. Then, the image processing unit 1a acquires the spectroscopic information from the total image information of the plurality of pieces of image information I2, and calculates spectroscopic image information B. For example, a spectrum of the spectroscopic image information B as shown in FIG. 9 is obtained.

In order to precisely acquire pulse waves, it is preferable that the period (period p) of the first light emission state be longer than the period (period q) of the second light emission state.

Next, in Step S112, the living body authenticity determination unit 1b determines, based on the brightness change information C, whether or not a pulse wave has been detected. Specifically, the living body authenticity determination unit 1b determines whether or not the amplitude of a specific frequency in the measurement data of the brightness change information C is higher than a predetermined value. Specifically, the specific frequency is a frequency of 0.5 Hz to 3 Hz. Then, when the amplitude is higher than the predetermined value, the living body authenticity determination unit 1b determines that a pulse wave has been detected, while when the amplitude is not more than the predetermined value it determines that a pulse wave cannot be detected. In the example of FIG. 17, since the amplitudes of "finger only" and "film A+finger" are both higher than the predetermined value, it is determined that a pulse wave has been detected. On the other hand, since the amplitude of "film B+finger" is not more than the predetermined value, it is determined that a pulse wave cannot be detected.

If determined as "Yes" in Step S112, then in Step S113, the living body authenticity determination unit 1b determines whether or not the spectrum of each of the spectroscopic image information A, B matches the living body determination spectrum (biogenic component combination). This determination is the same as the determination in Step S102 in FIG. 7.

If determined as "Yes" in Step S113, then in Step S114, the living body authenticity determination unit 1b determines that the measurement target 10a is a living body, and displays on the display unit 4 that the living body authenticity determination is "true".

If determined as "No" in Step S112 or Step S113, then in Step S115, the living body authenticity determination unit 1b determines that the measurement target 10a is not a living body, and displays on the display unit 4 that the living body authenticity determination is "false".

In the living body determination operation procedure described above, the order of Step S112 and Step S113 may be switched.

According to the living body determination device of the present exemplary embodiment, in addition to the effect described in the first exemplary embodiment, by performing pulse wave determination, for example, it becomes possible to eliminate a false finger with no vein that is fabricated by elaborately reproducing a fingerprint or a vein, and the accuracy of living body determination becomes further improved.

Also in the living body determination device of the present exemplary embodiment, the modification described in the first exemplary embodiment can be applied.

Second Application Example: Biometric Authentication Device

Next, a biometric authentication device to which the living body determination device of the second exemplary embodiment described above is applied will be described.

The biometric authentication device of the present example has a configuration similar to that of the biometric authentication device of the first application example described above. However, its biometric authentication operation differs in that pulse wave determination is performed.

Figure 18:
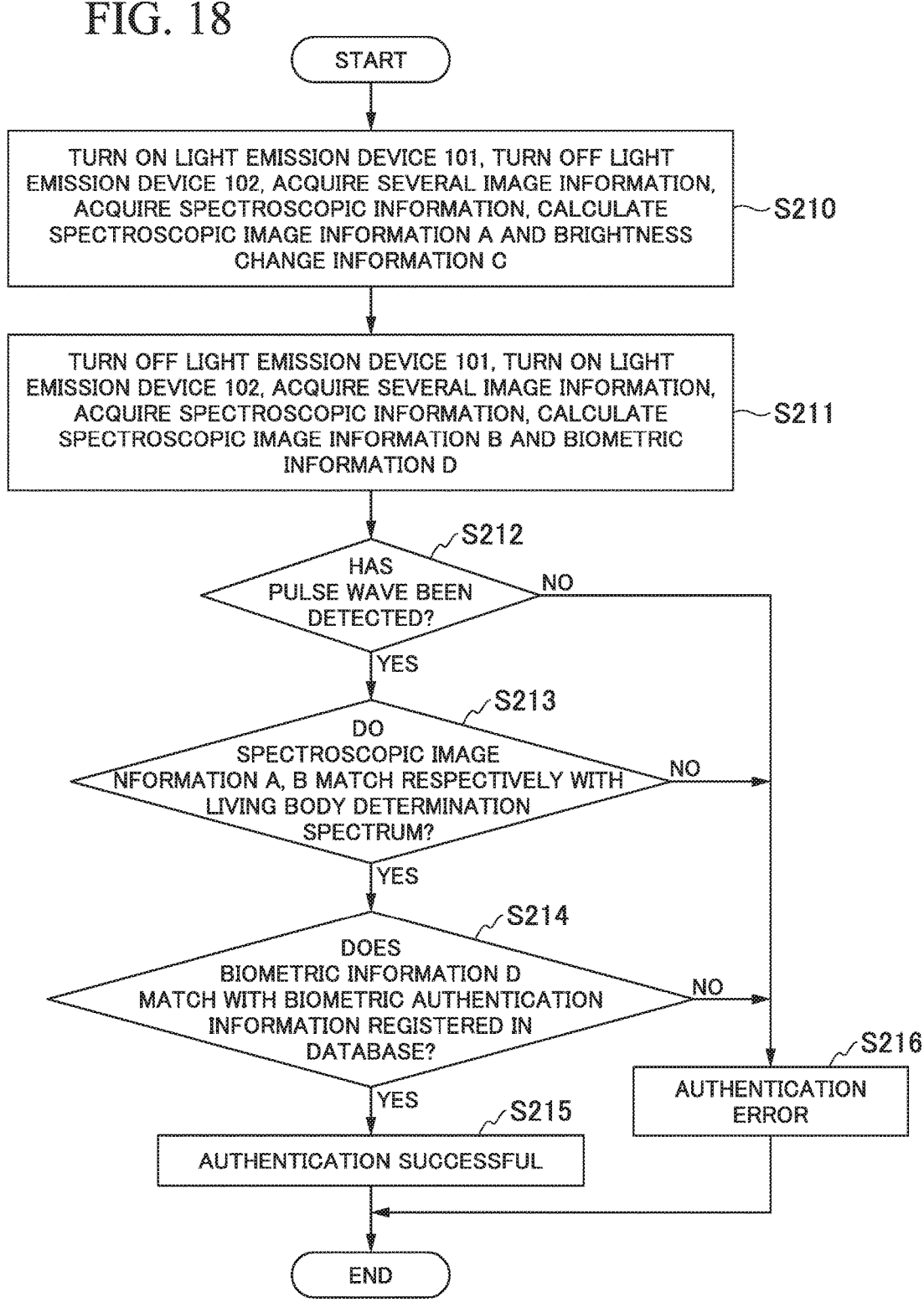
FIG. 18 is a flowchart showing a procedure of a biometric authentication operation of a biometric authentication device being a second application example to which the living body determination device of the second exemplary embodiment of the present invention is applied.

FIG. 18 shows a procedure of the biometric authentication operation. In this example, a white LED is used as the light emission device 101, a Fourier transform type spectroscopic device is used as the spectroscopic device 104, and a CMOS image sensor is used as the image acquisition device 105.

First, in Step S210, in the first light emission state where the light emission device 101 is turned on and the light emission device 102 is turned off, the image processing unit 11a controls the spectroscopic operation of the spectroscopic device 104 and acquires a plurality of pieces of image information related to the measurement target 10a from the image acquisition device 105. Then, the image processing unit 11a acquires spectroscopic information from the total image information of the plurality of pieces of acquired image information and calculates spectroscopic image information A, and also calculates brightness change information C from the plurality of pieces of acquired image information. This Step S210 is the same as Step S110 in FIG. 16.

In Step S211, in the second light emission state where the light emission device 101 is turned off and the light emission device 102 is turned on, the image processing unit 11a controls the spectroscopic operation of the spectroscopic device 104 and acquires a plurality of pieces of image information I2 related to the measurement target 10a from the image acquisition device 105. Then, the image processing unit 11a acquires the spectroscopic information from the total image information of the plurality of pieces of image information I2 and calculates spectroscopic image information B, and also calculates the biometric information D from the plurality of pieces of image information I2. This Step S211 is the same as Step S201 in FIG. 14.

In Step S212, the living body authenticity determination unit 11b determines, based on the brightness change information C, whether or not a pulse wave has been detected. This Step S212 is the same as Step S112 in FIG. 16.

If determined as "Yes" in Step S212, then in Step S213, the living body authenticity determination unit 11b determines whether or not the spectrum of each of the spectroscopic image information A, B matches the living body determination spectrum (biogenic component combination). This Step S213 is the same as Step S113 of FIG. 16 or Step S202 of FIG. 14.

If determined as "Yes" in Step S213, then in Step S214, the biometric authentication unit 11c acquires the biometric authentication information from the memory 12 and determines whether or not the biometric information D matches with the biometric authentication information. If the biometric information D matches with the biometric authentication information, then in Step S215, the biometric authentication unit 11c determines the user as being an authorized user, and displays on the display unit 4 information indicating that the authentication has been successful. These Steps S214, S215 are the same as Steps S203, S204 in FIG. 14.

If determined as "No" in any one of Steps S212 to S214, then in Step S216, the biometric authentication unit 11c determines the user as being an unauthorized user, and displays on the display unit 4 information indicating an authentication error.

In the biometric authentication operation described above, the order of Step S212 and Step S213 may be switched.

According to the biometric authentication device of the present example, by performing pulse wave determination, it is possible, in addition to the effect described in the first application example, to further improve reliability of biometric authentication while ensuring a high level of security.

Also in the biometric authentication device of the present example, the configuration and/or modification described in the first application example can be applied.

Third Exemplary Embodiment

Figure 19:
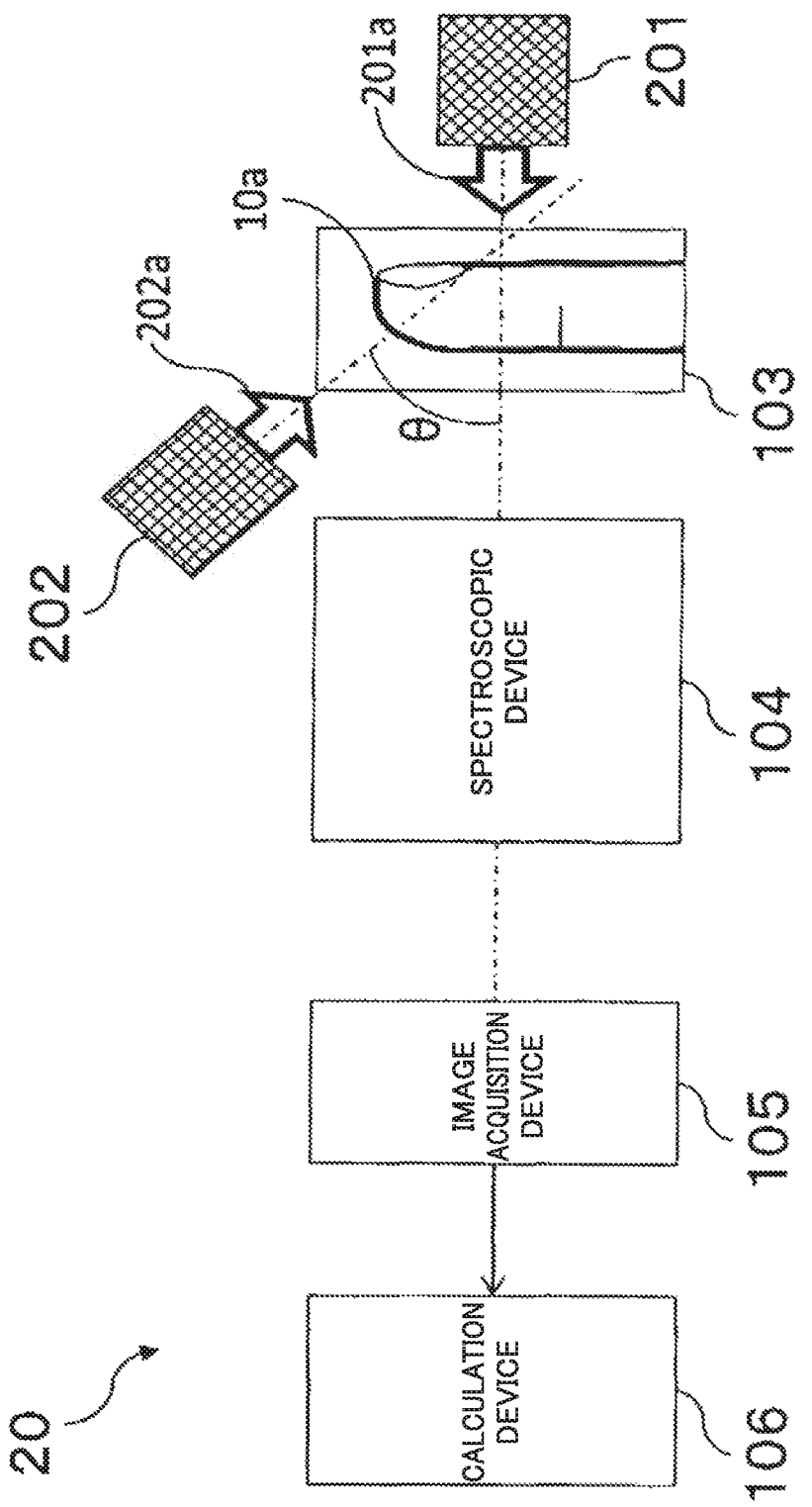
FIG. 19 is a block diagram showing a configuration of a living body determination device according to a third exemplary embodiment of the present invention.

FIG. 19 is a block diagram showing a configuration of a living body determination device according to a third exemplary embodiment of the present invention.

Referring to FIG. 19, a living body determination device 20 has light emission devices 201, 202, a measurement target placement device 103, a spectroscopic device 104, an image acquisition device 105, and a calculation device 106. The measurement target placement device 103, the spectroscopic device 104, the image acquisition device 105, and the calculation device 106 are the same as those described in the first exemplary embodiment. Hereunder, the configuration that differs from that of the first exemplary embodiment will be mainly described, and a description of the same configuration will be omitted.

The light emission devices 201, 202 respectively correspond to the light emission devices 101, 102 described in the first exemplary embodiment, and are arranged as described in the first exemplary embodiment. The light emission devices 201, 202 are light sources having a plurality of spectra in the wavelength range from the visible light range to the near-infrared light range. However, the respective wavelength bands thereof are different.

Figure 20:
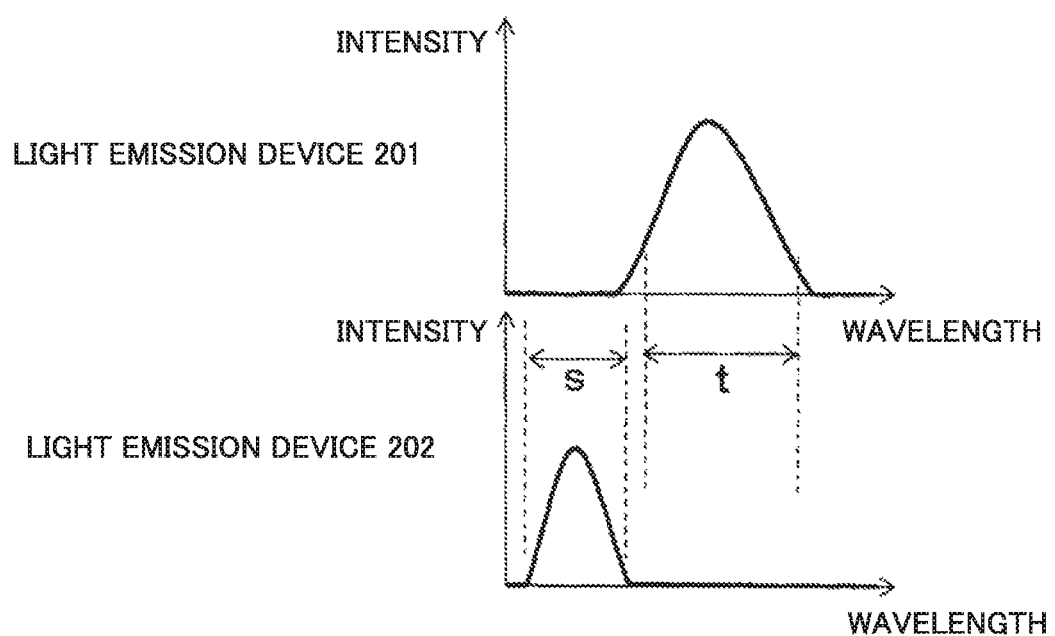
FIG. 20 is a diagram for explaining a wavelength band of each light emission device of the living body determination device shown in FIG. 19.

FIG. 20 shows wavelength bands of the light emission devices 201, 202. As shown in FIG. 20, the wavelength band t of the light emission device 201 is set to be longer than the wavelength band s of the light emission device 202. Although the wavelength band t and the wavelength band s may partially overlap with each other, it is more preferable that the wavelength band t and the wavelength band s be set so as not to overlap with each other. For example, the wavelength band s is in the proximity of 400 to 600 nm and the wavelength band t is in the proximity of 550 to 1000 nm. However, the present invention is not limited to this example.

The light emission device 201 may be configured with a combination of a white LED and a short-wavelength cut filter, and the light emission device 202 may be configured with a blue LED. As the short-wavelength cut filter, for example, a long pass filter having a characteristic of transmitting light of 550 nm or longer may be used. Note that the light emission devices 201, 202 are not limited to these configurations.

Next, the living body determination operation of the living body determination device 20 will be described in detail.

Figure 21:
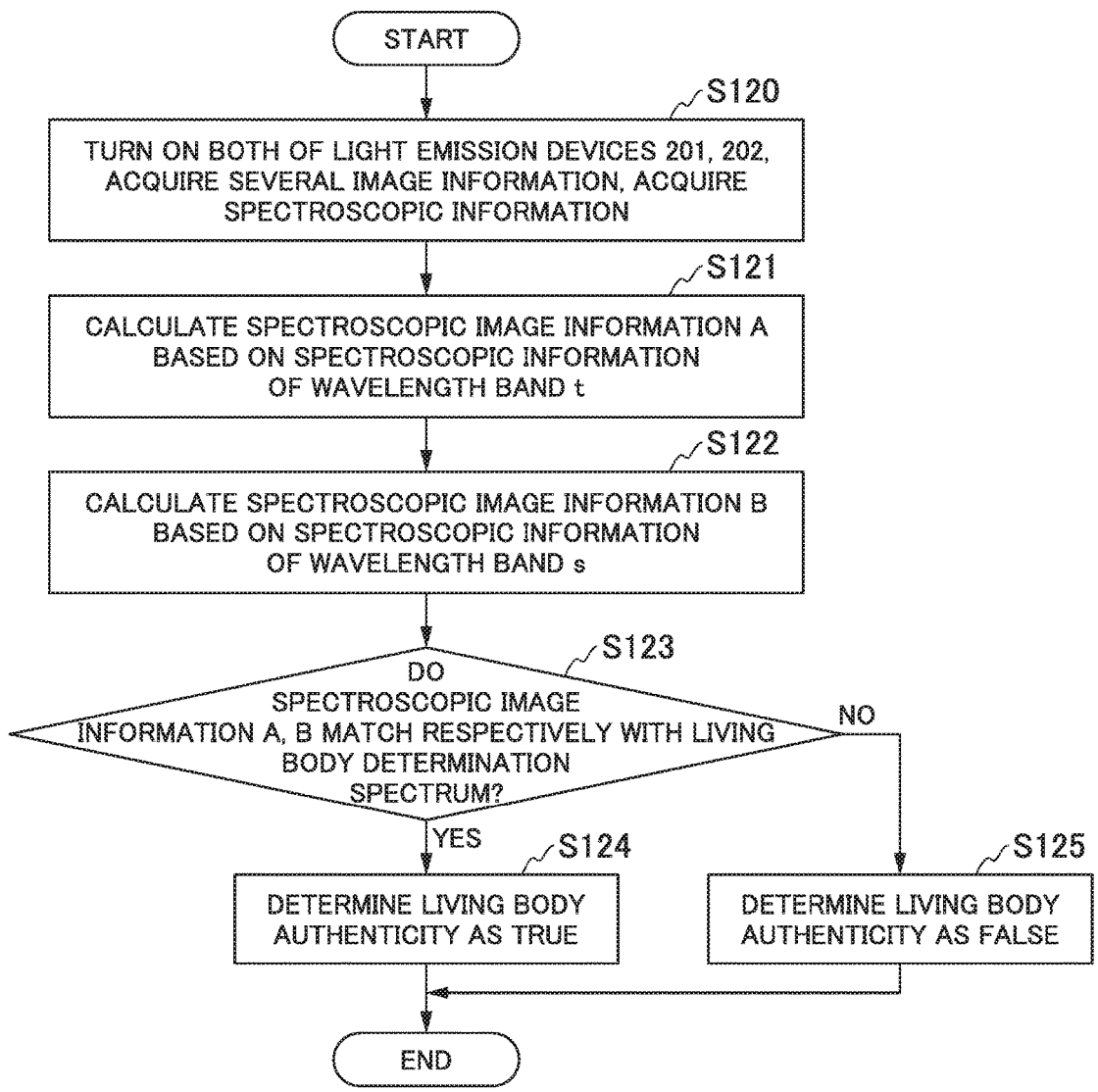
FIG. 21 is a flowchart showing a procedure of a living body determination operation of the living body determination device shown in FIG. 19.

FIG. 21 shows a procedure of the living body determination operation.

First, in Step S120, in the state where the light emission devices 201, 202 are both turned on, the image processing unit 1a controls the spectroscopic operation of the spectroscopic device 104 and acquires a plurality of pieces of image information related to the measurement target 10a from the image acquisition device 105. Then, the image processing unit 1a acquires the spectroscopic information based on the total image information of the plurality of pieces of image information.

In Step S121, the image processing unit 1a calculates the spectroscopic image information A indicating the transmission spectrum from the measurement target 10a, based on the spectroscopic information related to the wavelength band t in the spectroscopic information acquired in Step S120. Here, the transmission spectrum from the measurement target 10a is derived from the internal absorption spectrum of the measurement target 10a.

In Step S122, the image processing unit 1a calculates the spectroscopic image information B indicating the reflection spectrum from the measurement target 10a, based on the spectroscopic information related to the wavelength band s in the spectroscopic information acquired in Step S120. Here, the reflection spectrum from the measurement target 10a is derived from the absorption spectrum in the vicinity of the surface of the measurement target 10a.

In Step S123, the living body authenticity determination unit 1b determines whether or not the spectra of each of the spectroscopic image information A, B matches the spectrum for living body determination (biogenic component combination). Specifically, the living body authenticity determination unit 1b calculates a correlation degree between the spectrum of each of the spectroscopic image information A, B and the spectrum for living body determination, and determines whether or not the degree of correlation is not less than a predetermined value. This determination processing is basically the same as the determination processing in Step S102 in FIG. 7.

If determined as "Yes" in Step S123, then in Step S124, the living body authenticity determination unit 1b determines that the measurement target 10a is a living body, and displays on the display unit 4 that the living body authenticity determination is "true".

If determined as "No" in Step S123, then in Step S125, the living body authenticity determination unit 1b determines that the measurement target 10a is not a living body, and displays on the display unit 4 that the living body authenticity determination is "false".

In the living body determination operation described above, the order of Step S121 and Step S122 may be switched.

According to the living body determination device 20 of the present exemplary embodiment, in addition to the effect described in the first exemplary embodiment, it is possible to acquire the spectroscopic image information A, B by simultaneously lighting the illumination devices 201, 202 with different wavelength bands. Therefore it is possible to reduce the amount of time for measuring image information required for living body determination. As a result, it is possible to improve the operation efficiency.

In the living body determination device 20, the light emission devices 201, 202 can be referred to respectively as first and second light emission means, the spectroscopic device 104 can be referred to as spectroscopic means, and the image acquisition device 105 can be referred to as image acquisition means. Each of the first and second light emission means may include a plurality of light emission devices.

Also in the living body determination device of the present exemplary embodiment, the modification described in the first exemplary embodiment can be applied.

Third Application Example: Biometric Authentication Device

Next, a biometric authentication device to which the living body determination device of the third exemplary embodiment described above is applied will be described. The calculation device 106 of the biometric authentication device of the present example also has the configuration shown in FIG. 12.

Figure 22:
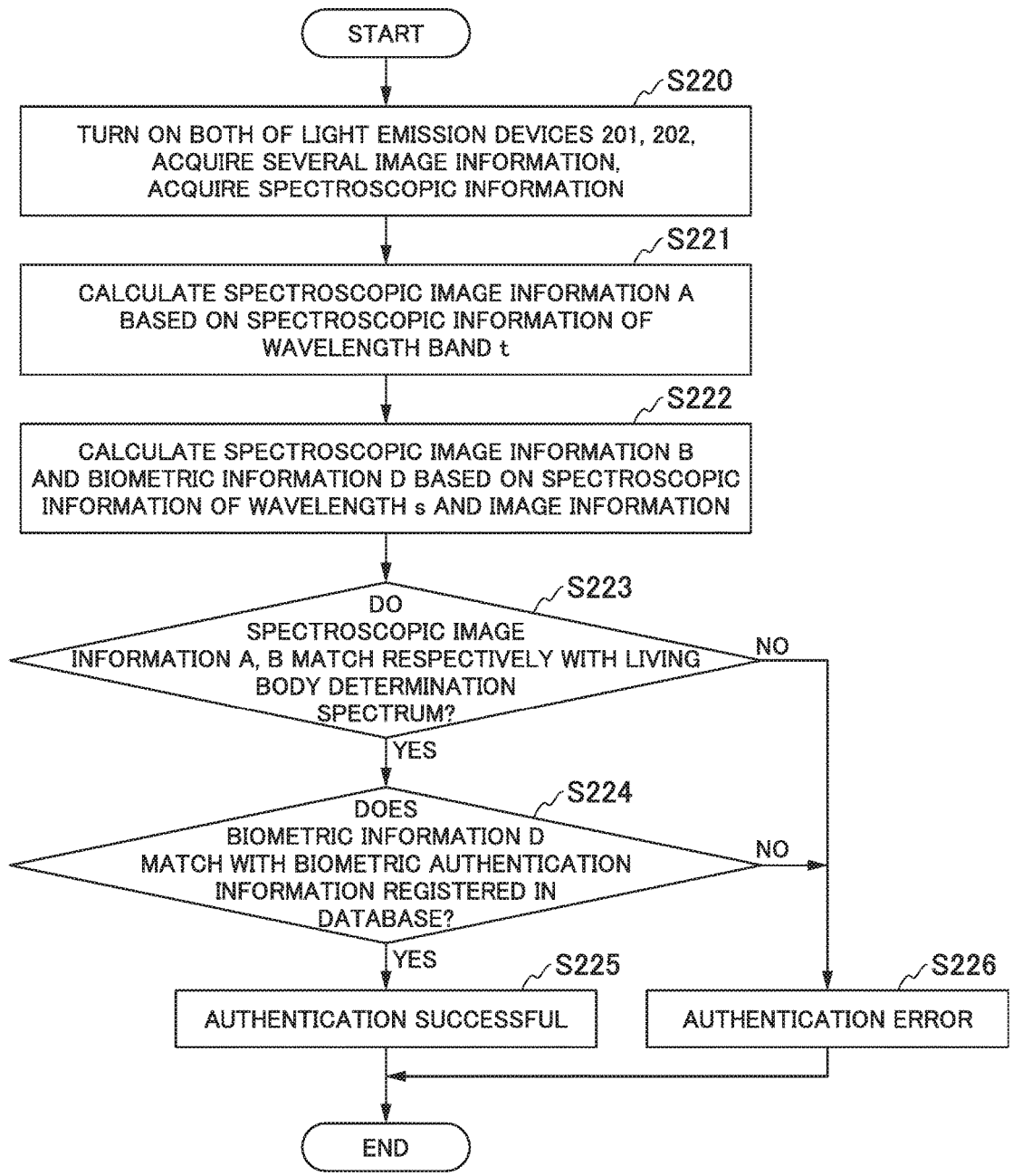
FIG. 22 is a flowchart showing a procedure of a biometric authentication operation of a biometric authentication device being a third application example to which the living body determination device of the third exemplary embodiment of the present invention is applied.

FIG. 22 shows a procedure of the biometric authentication operation.

First, in Step 220, in the state where the light emission devices 201, 202 are both turned on, the image processing unit 11a controls the spectroscopic operation of the spectroscopic device 104 and acquires a plurality of pieces of image information related to the measurement target 10a from the image acquisition device 105. Then, the image processing unit 11a acquires the spectroscopic information based on the total image information of the plurality of pieces of image information.

In Step S221, the image processing unit 11a calculates the spectroscopic information A based on the spectroscopic information related to the wavelength band t in the spectroscopic information acquired in Step S220. The calculation of the spectroscopic image information A is the same as that in Step S121 shown in FIG. 21.

In Step S222, the image processing unit 11a calculates the spectroscopic information B based on the spectroscopic information related to the wavelength band s in the spectroscopic information acquired in Step S220. Furthermore, the image processing unit 11a calculates the biometric information D related to the depressions and protrusions on the surface of the measurement target 10a, based on the plurality of pieces of image information related to the wavelength band s acquired in Step S220. The calculation of the spectroscopic image information B is the same as that in Step S122 shown in FIG. 21. The calculation of the biometric information D is basically the same as the calculation of the biometric information D in Step S201 in FIG. 14.

In Step S223, the living body authenticity determination unit 11b determines whether or not the spectra of each of the spectroscopic image information A, B matches the spectrum for living body determination. This determination is the same as that in Step S123 in FIG. 21.

If determined as "Yes" in Step S223, then in Step S224, the biometric authentication unit 11c acquires the biometric authentication information from the memory 12 and determines whether or not the biometric information D matches with the biometric authentication information. This biometric authentication determination is the same as that in Step S203 in FIG. 14.

If determined as "Yes" in Step S224, then in Step S225, the biometric authentication unit 11c determines the user as being an authorized user, and displays on the display unit 4 information indicating that the authentication has been successful. If determined as "No" in Step S223 or in Step S224, then in Step S226, the biometric authentication unit 11c determines the user as being an unauthorized user, and displays on the display unit 4 information indicating an authentication error. These processes for successful authentication and authentication error are the same as those in Steps S204, S205 in FIG. 14.

According to the biometric authentication device of the present example, in addition to the effect described in the first application example, the biometric information D is calculated using only the short wavelength side of the spectroscopic information. Therefore the influence of diffused light inside the living body can be eliminated, and the depression and protrusion information can be acquired more accurately.

Note that pulse wave determination using the brightness change information C described in the second exemplary embodiment may be performed in the living body determination device of the present exemplary embodiment, and in the biometric authentication device which is an application example thereof. In this case, in Step S121 (or in Step S221), the image processing unit 1a (or the image processing unit 11a) calculates brightness change information C based on the plurality of pieces of image information acquired in Step S120 (or in Step S220). Then, before or after Step S213 (or Step S223), the living body authenticity determination unit 1b (the living body authenticity determination unit 11b) determines, based on the brightness change information C, whether or not a pulse wave has been detected. This pulse wave determination is the same as that in Step S112 in FIG. 16.

Also in the biometric authentication device of the present example, the configuration and/or modification described in the first application example can be applied.

Fourth Exemplary Embodiment

Figure 23:
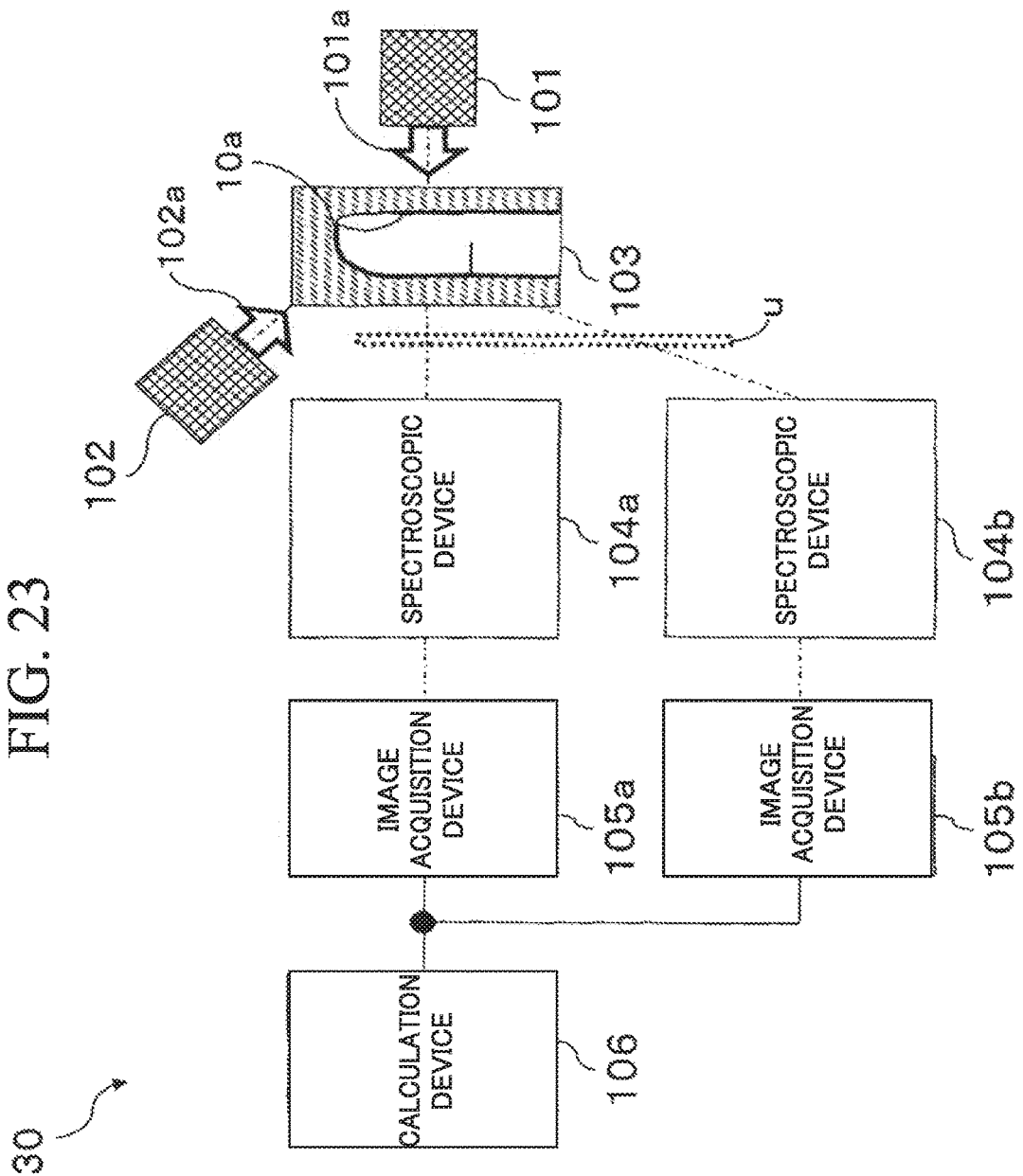
FIG. 23 is a block diagram showing a configuration of a living body determination device according to a fourth exemplary embodiment of the present invention.

FIG. 23 is a block diagram showing a configuration of a living body determination device according to a fourth exemplary embodiment of the present invention.

Referring to FIG. 23, a living body determination device 30 has light emission devices 101, 102, a measurement target placement device 103, spectroscopic devices 104a, 104b, image acquisition devices 105a, 105b, and a calculation device 106. The light emission devices 101, 102, the measurement target placement device 103, and the calculation device 106 are the same as those described in the first exemplary embodiment. Hereunder, the configuration that differs from that of the first exemplary embodiment will be mainly described, and a description of the same configuration will be omitted.

The spectroscopic devices 104a, 104b are respectively similar to the spectroscopic device 104 described in the first exemplary embodiment. The light emission device 104a is disposed at a position facing the light emission device 101 with the pedestal therebetween, so as to be oriented toward the first direction. The spectroscopic device 104b is disposed so as to be oriented toward a second direction that differs from the first direction.

Figure 24:
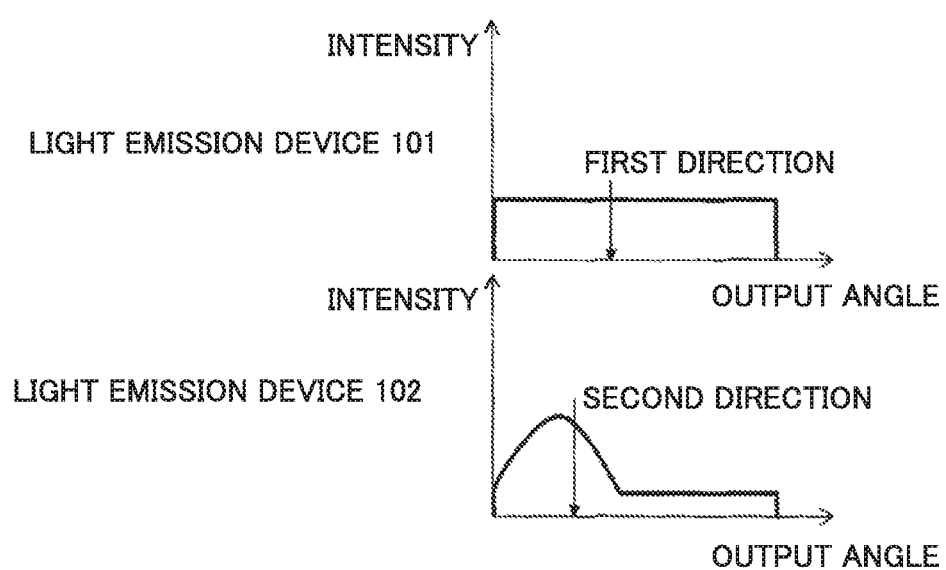
FIG. 24 is a diagram for explaining an operation of each light emission device of the living body determination device shown in FIG. 23.

FIG. 24 shows directions, at a position u, of lights originating from each of the light emission devices 101, 102. Since the light originating from the light emission device 101 is strongly diffused inside the living body, light is output in various directions. The light originating from the light irradiation device 102 has direction dependency because it involves reflection near the surface of the living body and diffusion inside the living body. The direction in which the reflection component on the living body surface is observed is the second direction and the direction in which the reflection component on the living body surface is not observed is the first direction.

The image acquisition devices 105a, 105b are respectively similar to the image acquisition device 105 described in the first exemplary embodiment. The image acquisition device 105a performs conversion into brightness information according to the intensity of the light output from the spectroscopic device 104a, and acquires a plurality of pieces of image information indicating brightness/darkness of brightness. The image acquisition device 105b performs conversion into brightness information according to the intensity of the light output from the spectroscopic device 301, and acquires a plurality of pieces of image information indicating brightness/darkness of brightness.

Next, the living body determination operation of the living body determination device 30 will be described in detail.

Figure 25:
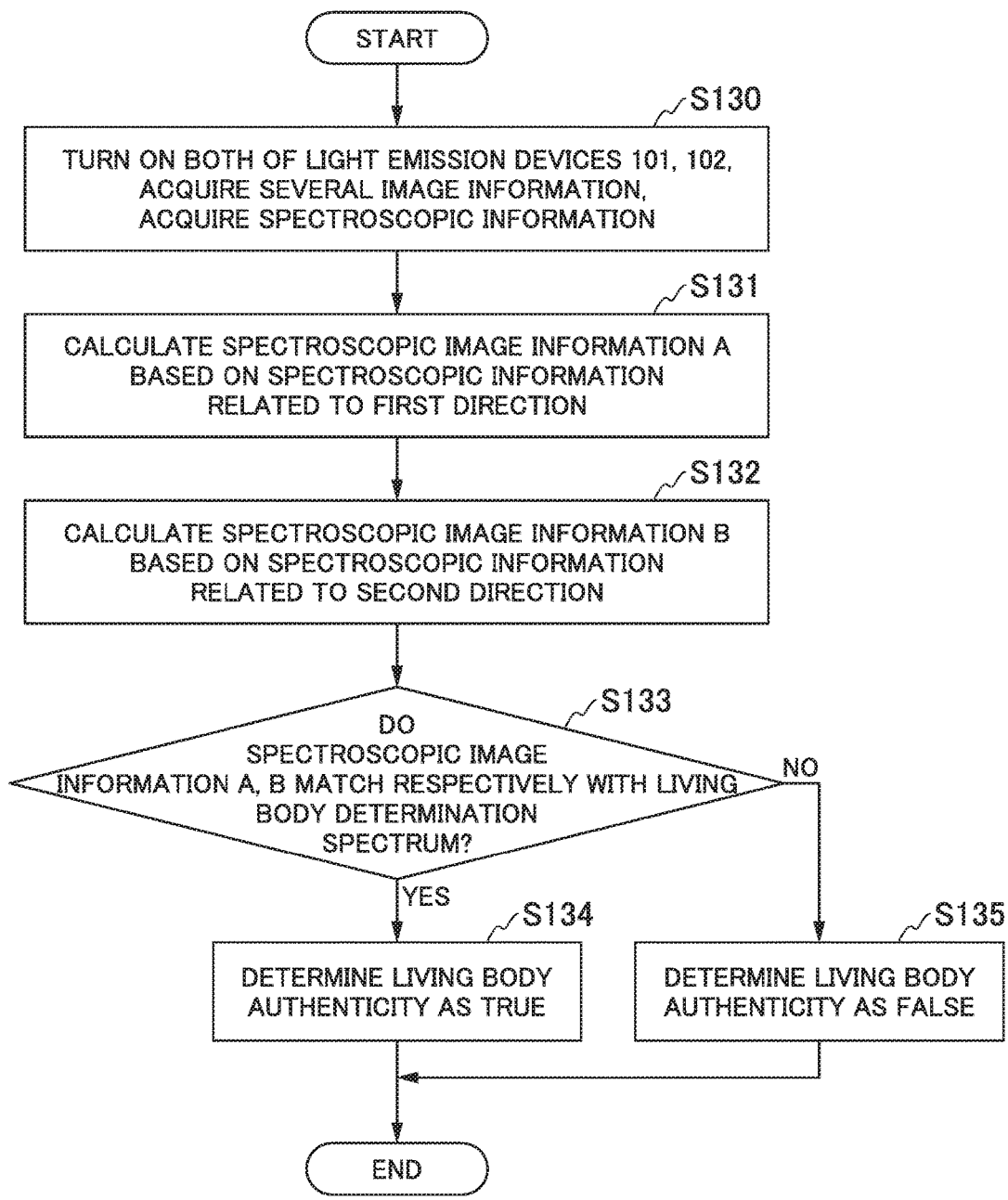
FIG. 25 is a flowchart showing a procedure of a living body determination operation of the living body determination device shown in FIG. 23.

FIG. 25 shows a procedure of the living body determination operation.

First, in Step S130, in the state where the light emission devices 101, 102 are both turned on, the image processing unit 1a controls the spectroscopic operation of the spectroscopic devices 104a, 104b and acquires a plurality of pieces of image information related to the measurement target 10a from the image acquisition devices 105a, 105b respectively. Then, the image processing unit 1a acquires the spectroscopic information based on the total image information of the plurality of pieces of image information acquired respectively from the image acquisition devices 105a, 105b.

In Step S131, the image processing unit 1a calculates the spectroscopic image information A indicating the transmission spectrum from the measurement target 10a, based on the spectroscopic information acquired from the image acquisition device 105a. Here, the transmission spectrum from the measurement target 10a is derived from the internal absorption spectrum of the measurement target 10a.

In Step S132, the image processing unit 1a calculates the spectroscopic image information B indicating the reflection spectrum from the measurement target 10a, based on the spectroscopic information acquired from the image acquisition device 105b. Here, the reflection spectrum of the measurement target 10a is derived from the absorption spectrum in the vicinity of the surface of the measurement target 10a.

In Step S133, the living body authenticity determination unit 1b determines whether or not the spectra of each of the spectroscopic image information A, B matches the spectrum for living body determination (biogenic component combination). Specifically, the living body authenticity determination unit 1b calculates a correlation degree between the spectrum of each of the spectroscopic image information A, B and the spectrum for living body determination, and determines whether or not the degree of correlation is not less than a predetermined value. This determination processing is basically the same as the determination processing in Step S102 in FIG. 7.

If determined as "Yes" in Step S133, then in Step S134, the living body authenticity determination unit 1b determines that the measurement target 10a is a living body, and displays on the display unit 4 that the living body authenticity determination is "true".

If determined as "No" in Step S133, then in Step S135, the living body authenticity determination unit 1b determines that the measurement target 10a is not a living body, and displays on the display unit 4 that the living body authenticity determination is "false".

In the living body determination operation described above, the order of Step S131 and Step S132 may be switched.

According to the living body determination device 30 of the present exemplary embodiment, in addition to the effect described in the first exemplary embodiment, it is possible to acquire the spectroscopic image information A, B by simultaneously detecting the lights originating from the light emission devices 101, 102 separately according to the directions thereof. As a result, the amount of time for measuring the image information required for living body determination can be reduced, and the operation efficiency can be improved.

In the living body determination device 30, the light emission devices 101, 102 can be referred to respectively as first and second light emission means, the spectroscopic devices 104a, 104b can be referred to respectively as first and second spectroscopic means, and the image acquisition devices 105a, 105b can be referred to respectively as first and second image acquisition means. Each of the first and second light emission means may include a plurality of light emission devices.

Also in the living body determination device 30 of the present exemplary embodiment, the modification described in the first exemplary embodiment can be applied.

Fourth Application Example: Biometric Authentication Device

Next, a biometric authentication device to which the living body determination device of the fourth exemplary embodiment described above is applied will be described. The calculation device 106 of the biometric authentication device of the present example also has the configuration shown in FIG. 12.

Figure 26:
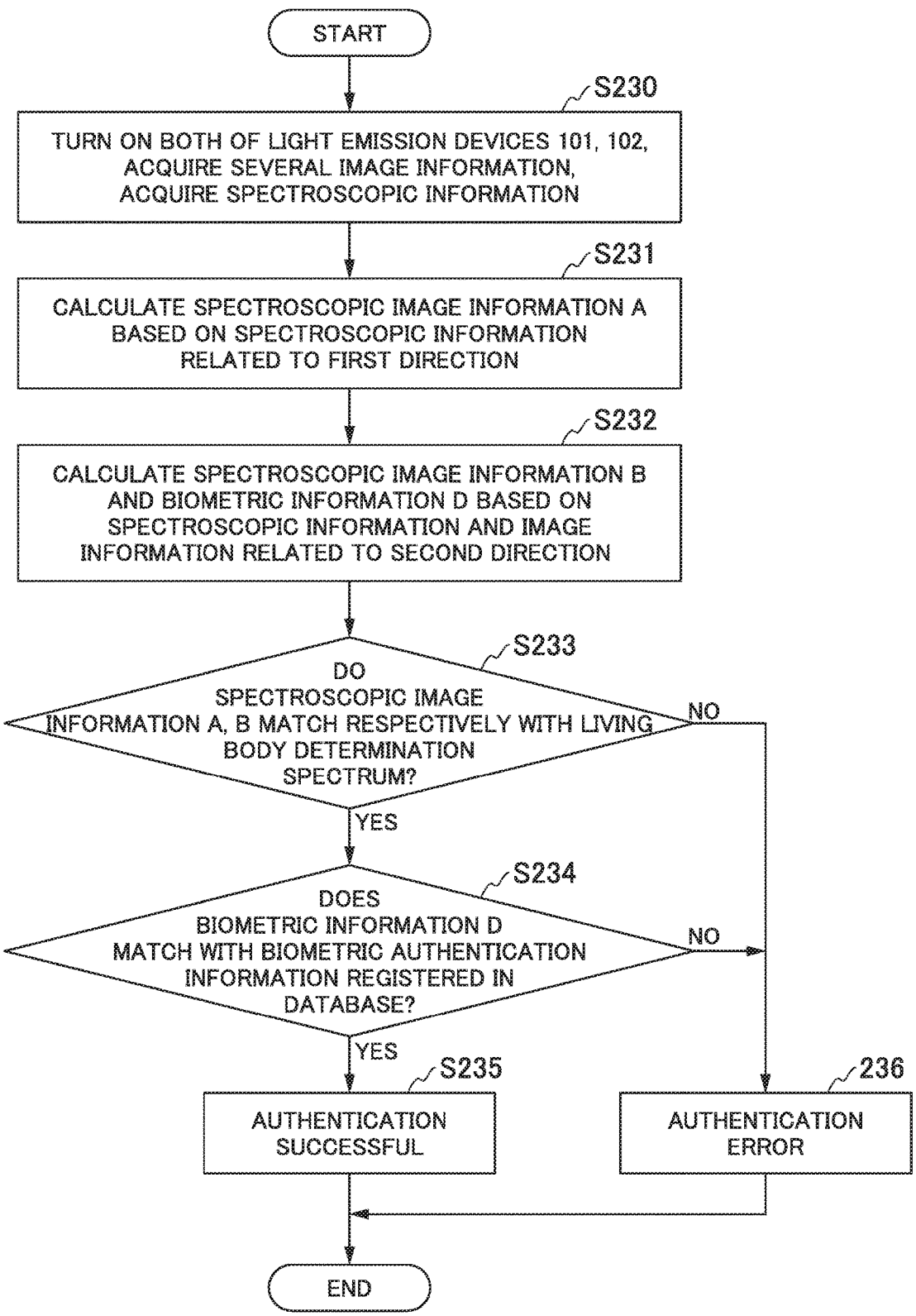
FIG. 26 is a flowchart showing a procedure of a biometric authentication operation of a biometric authentication device being a fourth application example to which the living body determination device of the fourth exemplary embodiment of the present invention is applied.

FIG. 26 shows a procedure of the biometric authentication operation.

In Step S230, in the state where the light emission devices 101, 102 are both turned on, the image processing unit 11a controls the spectroscopic operation of the spectroscopic devices 104a, 104b and acquires a plurality of pieces of image information related to the measurement target 10a from the image acquisition devices 105a, 105b respectively. Then, the image processing unit 11a acquires the spectroscopic information based on the total image information of the plurality of pieces of image information acquired respectively from the image acquisition devices 105a, 105b.

In Step S231, the image processing unit 11a calculates the spectroscopic image information A indicating the transmission spectrum from the measurement target 10a, based on the spectroscopic information acquired from the image acquisition device 105a. The calculation of the spectroscopic image information A is the same as that in Step S131 shown in FIG. 25.

In Step S232, the image processing unit 11a calculates the spectroscopic image information B indicating the reflection spectrum from the measurement target 10a, based on the spectroscopic information acquired from the image acquisition device 105b. Furthermore, the image processing unit 11a calculates the biometric information D related to the depressions and protrusions on the surface of the measurement target 10a, based on the plurality of pieces of image information acquired from the image acquisition device 105b. The calculation of the spectroscopic image information B is the same as that in Step S132 shown in FIG. 25. The calculation of the biometric information D is basically the same as the calculation of the biometric information D in Step S201 in FIG. 14.

In Step S233, the living body authenticity determination unit 11b determines whether or not the spectra of each of the spectroscopic image information A, B matches the spectrum for living body determination. This determination is the same as that in Step S133 in FIG. 25.

If determined as "Yes" in Step S233, then in Step S234, the biometric authentication unit 11c acquires the biometric authentication information from the memory 12 and determines whether or not the biometric information D matches with the biometric authentication information. This biometric authentication determination is the same as that in Step S203 in FIG. 14.

If determined as "Yes" in Step S234, then in Step S235, the biometric authentication unit 11c determines the user as being an authorized user, and displays on the display unit 4 information indicating that the authentication has been successful. If determined as "No" in Step S233 or in Step S234, then in Step S236, the biometric authentication unit 11c determines the user as being an unauthorized user, and displays on the display unit 4 information indicating an authentication error. These processes for successful authentication and authentication error are the same as those in Steps S204, S205 in FIG. 14.

According to the biometric authentication device of the present example, in addition to the effect similar to that of the first application example, the amount of time for measuring the image information required for living body determination can be reduced. Therefore it is possible to reduce the amount of time for the biometric authentication processing and improve the operation efficiency.

Note that pulse wave determination using the brightness change information C described in the second exemplary embodiment may be performed in the living body determination device of the present exemplary embodiment, and in the biometric authentication device which is an application example thereof. In this case, in Step S131 (or in Step S231), the image processing unit 1a (or the image processing unit 11a) calculates brightness change information C based on the plurality of pieces of image information acquired in Step S130 (or in Step S230). Then, before or after Step S133 (or Step S233), the living body authenticity determination unit 1b (the living body authenticity determination unit 11b) determines, based on the brightness change information C, whether or not a pulse wave has been detected. This pulse wave determination is the same as that in Step S112 in FIG. 16.

Also in the biometric authentication device of the present example, the configuration and/or modification described in the first application example can be applied.

Fifth Exemplary Embodiment

Figure 27:
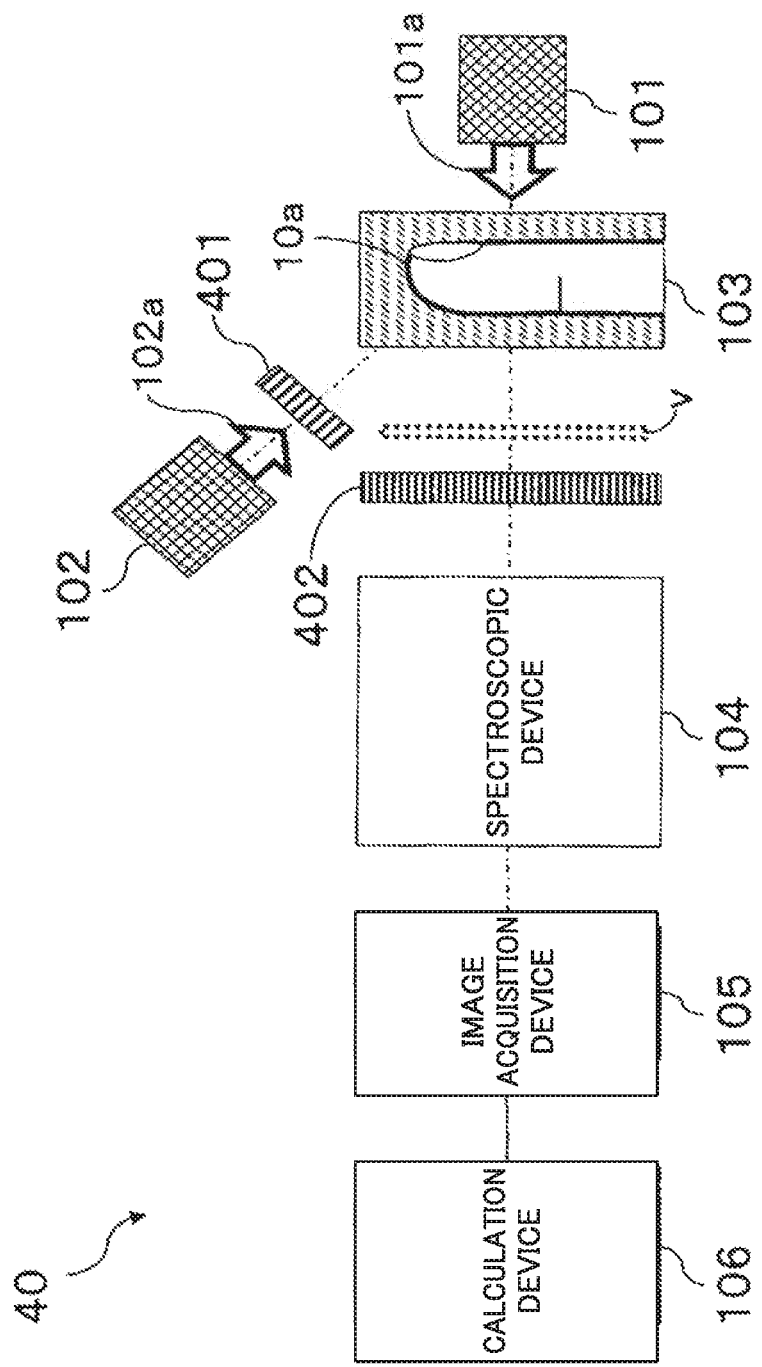
FIG. 27 is a block diagram showing a configuration of a living body determination device according to a fifth exemplary embodiment of the present invention.

FIG. 27 is a block diagram showing a configuration of a living body determination device according to a fifth exemplary embodiment of the present invention.

Referring to FIG. 27, a living body determination device 40 has light emission devices 101, 102, a measurement target placement device 103, a spectroscopic device 104, an image acquisition device 105, a calculation device 106, and polarization control devices 401, 402. The light emission devices 101, 102, the measurement target placement device 103, the spectroscopic device 104, the image acquisition device 105, and the calculation device 106 are basically the same as those described in the first exemplary embodiment. Hereunder, the configuration that differs from that of the first exemplary embodiment will be mainly described, and a description of the same configuration will be omitted.

Each of the polarization control devices 401, 402 is a device for controlling the polarization state of light. For example, there may be applied one composed of an optical polarizer, one composed of a combination of an optical polarizer and a phase difference plate, or one composed of a combination of an optical polarizer and a liquid crystal cell.

The polarization control device 401 is disposed between the light emission device 102 and the pedestal of the measurement target placement device 103, and controls the polarization state of light output from the light emission device 102. Here, the polarization control device 401 controls light output from the light emission device 102 into s-polarized light.

The polarization control device 402 is arranged between the spectroscopic device 104 and the pedestal, and controls the polarization state of light traveling from the vicinity of the pedestal toward the spectroscopic device 104 into specific polarization states (first polarized light and second polarized light). The polarization control device 402 can switch between a first state where the first polarized light is output and a second state where the second polarized light is output. Here, for example, the second polarized light is a polarized light parallel to the s-polarized light, and the first polarized light is a polarized light orthogonal to the second polarized light.

In the case where the polarization control device 402 is configured with an optical polarizer only, the state where the transmissive axis of the optical polarizer is parallel to the first polarized light is the first state. The state where the optical polarizer is rotated by 90° from this first state is the second state.

In the case where the polarization control device 402 is configured with a combination of an optical polarizer and a phase difference plate (for example, ½ wavelength plate), the state where the transmissive axis of the optical polarizer and the optical axis of the phase difference plate are both parallel to the first polarized light is the first state. The state where the phase difference plate is rotated by 45° from this first state is the second state.

In the case where the polarization control device 402 is configured with a combination of an optical polarizer and a liquid crystal cell (for example, a TN cell), the state where no voltage is applied to the liquid crystal cell is the first state, and the state where a voltage is applied to the liquid crystal cell is the second state. In the first state, the optical axis of the first layer of the liquid crystal cell is parallel or orthogonal to the first polarized light, and the transmissive axis of the optical polarizer is parallel to the optical axis of the final layer of the liquid crystal cell (perpendicular to the optical axis of the first layer). Therefore, the polarized light rotates in the liquid crystal cell and the first polarized light passes through the optical polarizer. In the second state, a voltage is applied to the liquid crystal cell. Therefore the polarized light does not rotate in the liquid crystal cell, and the second polarized light passes through the optical polarizer.

In addition to the above, the polarization control device 402 may be of a configuration to perform polarization control within a plane by means of a photonic crystal or the like.

As with the first exemplary embodiment, the calculation device 106 has a configuration shown in FIG. 3, and the control unit 1 (image processor 1a) controls the polarization control operation of the polarization control devices 401, 402.

Figure 28:
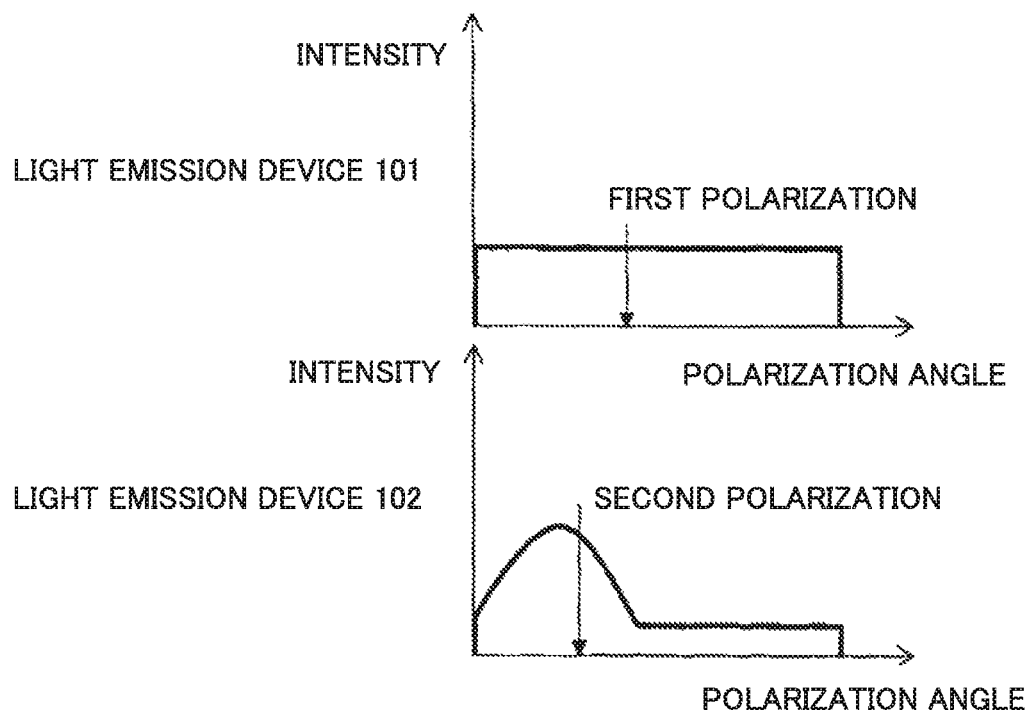
FIG. 28 is a diagram for explaining an operation of each light emission device of the living body determination device shown in FIG. 27.

FIG. 28 shows relationships between polarization angle and intensity at a position v related to light originating from each of the light emission devices 101, 102. Since the light originating from the light emission device 101 is strongly diffused inside the living body, the light is in a state of not being polarized. The light originating from the light emission device 102 has direction dependency because it involves reflection near the surface of the living body and diffusion inside the living body. The direction in which the reflection component on the living body surface is observed is the second polarization, and the direction in which the reflection component on the living body surface is not observed is the first polarization.

The spectroscopic device 104 receives the light whose polarization is controlled by the polarization control device 402, and divides it into intensities corresponding to the wavelength of the light, or changes the phase of the light, and outputs it toward the image acquisition device 105. The image acquisition device 105 performs conversion into brightness information according to the intensity of the light output from the spectroscopic device 104, and acquires a plurality of pieces of image information indicating brightness/darkness of brightness. Note that the polarization control device 402 may be installed between the spectroscopic device 104 and the image acquisition device 105.

Next, the living body determination operation of the living body determination device 40 will be described in detail.

Figure 29:
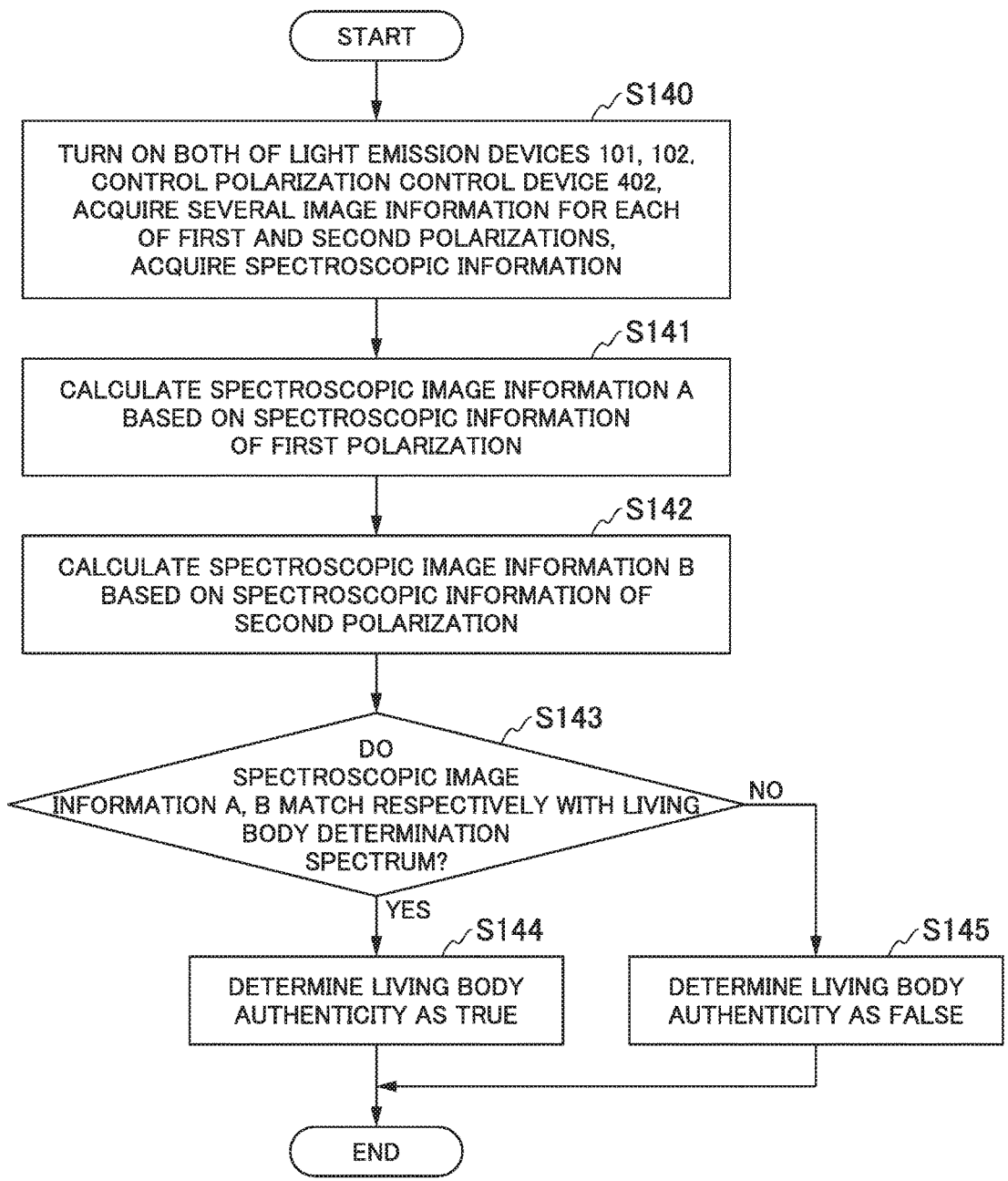
FIG. 29 is a flowchart showing a procedure of a living body determination operation of the living body determination device shown in FIG. 27.

FIG. 29 shows a procedure of the living body determination operation.

In Step S140, the image processing unit 1a turns on both of the light emission devices 101, 102, controls both of the spectroscopic device 402 and the spectroscopic device 104, and acquires, for each of the first and second polarizations, a plurality of pieces of image information from the image acquisition device 105. Then, the image processing unit 1a acquires, for each of the first and second polarizations, the spectroscopic information, based on the total image information of the plurality of pieces of image information.

In Step S141, the image processing unit 1a calculates the spectroscopic image information A indicating the transmission spectrum from the measurement target 10a, based on the spectroscopic information of the first polarization acquired from the image acquisition device 105. Here, the transmission spectrum from the measurement target 10a is derived from the internal absorption spectrum of the measurement target 10a.

In Step S142, the image processing unit 1a calculates the spectroscopic image information B indicating the reflection spectrum from the measurement target 10a, based on the spectroscopic information of the second polarization acquired from the image acquisition device 105. Here, the reflection spectrum from the measurement target 10a is derived from the absorption spectrum in the vicinity of the surface of the measurement target 10a.

In Step S143, the living body authenticity determination unit 1b determines whether or not the spectra of each of the spectroscopic image information A, B matches the spectrum for living body determination (biogenic component combination). Specifically, the living body authenticity determination unit 1b calculates a correlation degree between the spectrum of each of the spectroscopic image information A, B and the spectrum for living body determination, and determines whether or not the degree of correlation is not less than a predetermined value. This determination processing is basically the same as the determination processing in Step S102 in FIG. 7.

If determined as "Yes" in Step S143, then in Step S144, the living body authenticity determination unit 1b determines that the measurement target 10a is a living body, and displays on the display unit 4 that the living body authenticity determination is "true".

If determined as "No" in Step S143, then in Step S145, the living body authenticity determination unit 1b determines that the measurement target 10a is not a living body, and displays on the display unit 4 that the living body authenticity determination is "false".

In the living body determination operation described above, the order of Step S141 and Step S142 may be switched.

According to the living body determination device 40 of the present exemplary embodiment, in addition to the effect described in the first exemplary embodiment, it is possible to acquire the spectroscopic image information A, B by simultaneously detecting the lights originating from the light emission devices 101, 102 respectively according to the polarization directions thereof. Hence the amount of time for measuring the image information required for living body determination can be reduced, and as a result the operation efficiency can be improved.

In the above described living body determination device 40, the light emission devices 101, 102 can be referred to respectively as first and second light emission means, the spectroscopic device 104 can be referred to as spectroscopic means, and the image acquisition device 105 can be referred to as image acquisition means. Each of the first and second light emission means may include a plurality of light emission devices.

Also in the living body determination device 40 of the present exemplary embodiment, the modification described in the first exemplary embodiment can be applied.

Fifth Application Example: Biometric Authentication Device

Next, a biometric authentication device to which the living body determination device of the fifth exemplary embodiment described above is applied will be described. The calculation device 106 of the biometric authentication device of the present example also has the configuration shown in FIG. 12.

Figure 30:
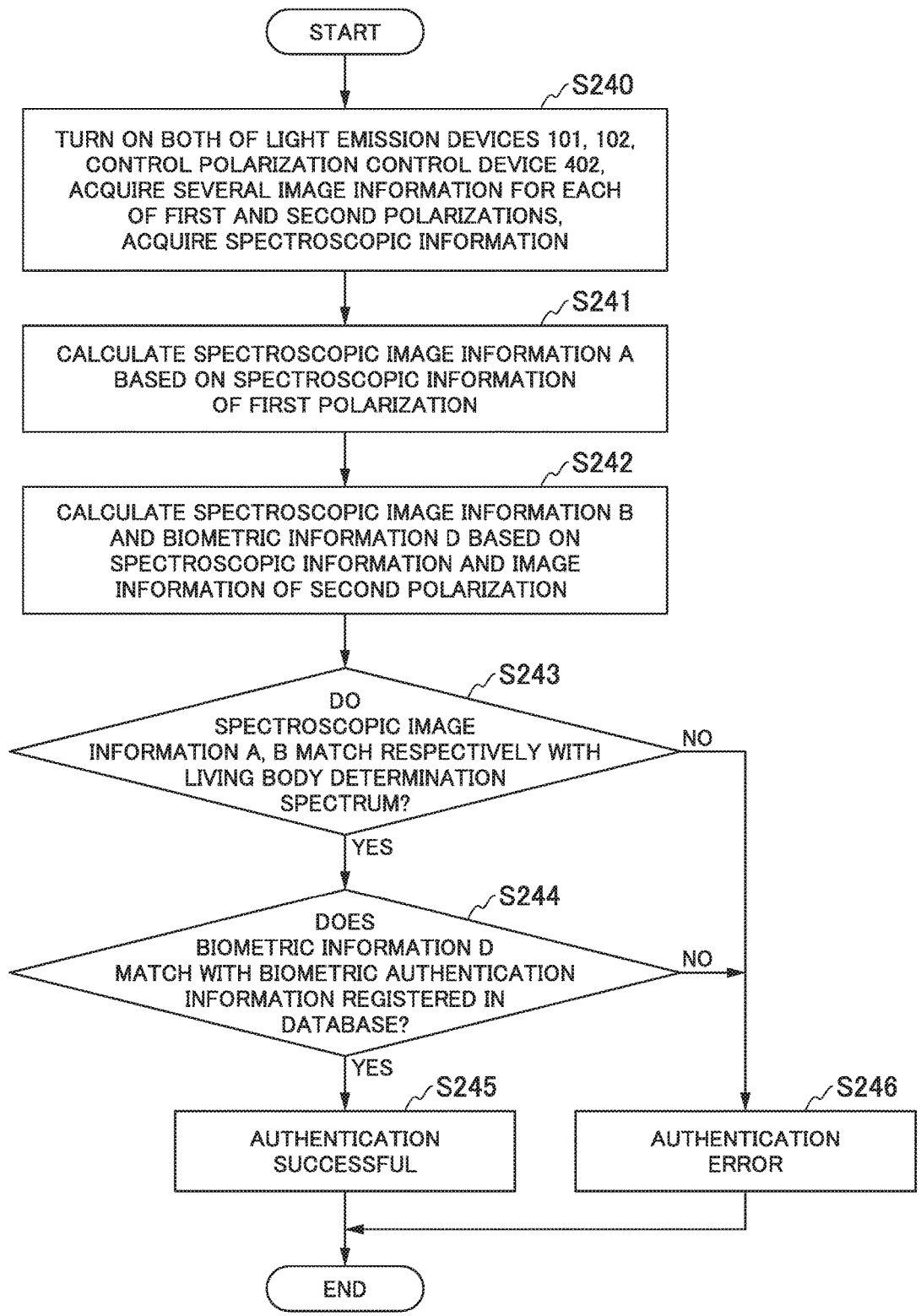
FIG. 30 is a flowchart showing a procedure of a biometric authentication operation of a biometric authentication device being a fifth application example to which the living body determination device of the fifth exemplary embodiment of the present invention is applied.

FIG. 30 shows a procedure of the biometric authentication operation.

In Step S240, the image processing unit 11a turns on both of the light emission devices 101, 102, controls both of the spectroscopic device 402 and the spectroscopic device 104, and acquires, for each of the first and second polarizations, a plurality of pieces of image information from the image acquisition device 105. Then, the image processing unit 11a acquires, for each of the first and second polarizations, the spectroscopic information, based on the total image information of the plurality of pieces of image information.

In Step S241, the image processing unit 11a calculates the spectroscopic image information A indicating the transmission spectrum from the measurement target 10a, based on the spectroscopic information of the first polarization acquired from the image acquisition device 105. The calculation of the spectroscopic image information A is the same as that in Step S141 shown in FIG. 29.

In Step S242, the image processing unit 11a calculates the spectroscopic image information B indicating the reflection spectrum from the measurement target 10a, based on the spectroscopic information of the second polarization acquired from the image acquisition device 105. Furthermore, the image processing unit 11a calculates the biometric information D related to the depressions and protrusions on the surface of the measurement target 10a, based on the plurality of pieces of image information of the second polarization acquired from the image acquisition device 105. The calculation of the spectroscopic image information B is the same as that in Step S142 shown in FIG. 29. The calculation of the biometric information D is basically the same as the calculation of the biometric information D in Step S201 in FIG. 14.

In Step S243, the living body authenticity determination unit 11b determines whether or not the spectra of each of the spectroscopic image information A, B matches the spectrum for living body determination. This determination is the same as that in Step S143 in FIG. 29.

If determined as "Yes" in Step S243, then in Step S244, the biometric authentication unit 11c acquires the biometric authentication information from the memory 12 and determines whether or not the biometric information D matches with the biometric authentication information. This biometric authentication determination is the same as that in Step S203 in FIG. 14.

If determined as "Yes" in Step S244, then in Step S245, the biometric authentication unit 11c determines the user as being an authorized user, and displays on the display unit 4 information indicating that the authentication has been successful. If determined as "No" in Step S243 or in Step S244, then in Step S246, the biometric authentication unit 11c determines the user as being an unauthorized user, and displays on the display unit 4 information indicating an authentication error. These processes for successful authentication and authentication error are the same as those in Steps S204, S205 in FIG. 14.

According to the biometric authentication device of the present example, in addition to the effect similar to that of the first application example, the amount of time for measuring the image information required for living body determination can be reduced. Therefore it is possible to reduce the amount of time for the biometric authentication processing and improve the operation efficiency.

Note that pulse wave determination using the brightness change information C described in the second exemplary embodiment may be performed in the living body determination device of the present exemplary embodiment, and in the biometric authentication device which is an application example thereof. In this case, in Step S141 (or in Step S241), the image processing unit 1a (or the image processing unit 11a) calculates brightness change information C based on the plurality of pieces of image information acquired in Step S140 (or in Step S240). Then, before or after Step S143 (or Step S243), the living body authenticity determination unit 1b (or the living body authenticity determination unit 11b) determines, based on the brightness change information C, whether or not a pulse wave has been detected. This pulse wave determination is the same as that in Step S112 in FIG. 16.

Also in the biometric authentication device of the present example, the configuration and/or modification described in the first application example can be applied.

The exemplary embodiments and application examples of the present invention have been described above as exemplary examples. However, the present invention is not limited to the exemplary embodiments and application examples described above, and various configurations that can be understood by those skilled in the art may be applied to the configuration and operation thereof.

In addition, the present invention may take forms such as the following notes 1 to 32, but it is not limited thereto.

[Supplementary Note 1]
A living body determination device comprising:
a pedestal for placing a measurement target;
a spectroscopic means that receives light entering from the pedestal side and disperses the light into intensities corresponding to wavelengths and outputs it;
a first light emission means that is provided at a position facing the spectroscopic means with the pedestal therebetween and emits first light having a plurality of spectra toward the pedestal;
a second light emission means that emits second light having a plurality of spectra toward the pedestal from the spectroscopic means side;
an image acquisition means that receives light output from the spectroscopic means and outputs image information indicating brightness corresponding to an intensity of the light; and
a control unit that acquires first image information related to the measurement target from the image acquisition means for each spectrum of the first light and acquires first spectroscopic information based on each first image information, the control unit acquiring second image information related to the measurement target from the image acquisition means for each spectrum of the second light and acquiring second spectroscopic information based on each second image information, and the control unit determining whether or not the measurement target is a living body based on comparison results between each of the first and second spectroscopic information and a predetermined spectral characteristic.

[Supplementary Note 2]
The living body determination device according to Supplementary Note 1, wherein the control unit determines whether or not the measurement target is a living body based on a correlation degree between each of the first and second spectroscopic information and the predetermined spectral characteristic.

[Supplementary Note 3]
The living body determination device according to Supplementary Note 1 or 2, wherein a wavelength band of the first light emission means and a wavelength band of the second light emission means are within a range from a visible light range to a near-infrared light range.

[Supplementary Note 4]
The living body determination device according to any one of Supplementary Notes 1 to 3, wherein a wavelength band of the first light emission means and a wavelength band of the second light emission means are within a range of 400 to 1000 nm.

[Supplementary Note 5]
The living body determination device according to any one of Supplementary Notes 1 to 4, wherein, in a state where the first light emission means is turned on and the second light emission means is turned off, the control unit acquires the first image information from the image acquisition means, and in a state where the second light emission means is turned on and the first light emission means is turned off, the control unit acquires the second image information from the image acquisition means.

[Supplementary Note 6]
The living body determination device according to any one of Supplementary Notes 1 to 4,
wherein a wavelength band of the first light emission means is set to a longer wavelength band than a wavelength band of the second light emission means, and
in a state where the first and second light emission means are both turned on, the control unit acquires the first and second image information from the image acquisition means.

[Supplementary Note 7]

The living body determination device according to Supplementary Note 6, wherein a wavelength band of the first light emission means is 550 to 1000 nm, and a wavelength band of the second light emission means is 400 to 600 nm.

[Supplementary Note 8]

The living body determination device according to any one of Supplementary Notes 1 to 4, wherein the spectroscopic means comprises:

a first spectroscopic device that is positioned on an optical axis of the first light emission means and receives transmitted light based on the first light from the measurement target; and a second spectroscopic device that is provided in a position facing the second light emission means with the optical axis therebetween and receives reflected light based on the second light from the measurement target, and the image acquisition means comprises:

a first image acquisition device that receives light output from the first spectroscopic means and outputs image information indicating brightness corresponding to an intensity of the light; and a second image acquisition device that receives light output from the second spectroscopic means and outputs image information indicating brightness corresponding to an intensity of the light, and in a state where the first and second light emission means are both turned on, the control unit acquires the first image information from the first image acquisition device and acquires the second image information from the second image acquisition device.

[Supplementary Note 9]

The living body determination device according to any one of Supplementary Notes 1 to 4, further comprising:

a first polarization control device that is provided between the second light emission means and the pedestal, the first polarization control device controlling a polarization state of the second light into a predetermined polarization; and a second polarization control device that is provided between the spectroscopic means and the pedestal, the second polarization control device controlling a polarization state of light entering from the pedestal side, and the second polarization control device being capable of switching between a first polarization control state where a first polarization is output and a second polarization control state where a second polarization orthogonal to the first polarization is output, wherein in a state where the first and second light emission means are both turned on, the control unit switches the second polarization control device into the first polarization control state and acquires the first image information from the image acquisition means, and switches the second polarization control device into the second polarization control state and acquires the second image information from the image acquisition means.

[Supplementary Note 10]

The living body determination device according to any one of Supplementary Notes 1 to 9, wherein the control unit calculates brightness change information indicating temporal changes in brightness, based on the first image information, the control unit determines that the measurement target has a pulse wave in a case where amplitude at a predetermined frequency of the brightness change information is higher than a predetermined value, and the control unit determines that the measurement target does not have a pulse wave in a case where amplitude at the predetermined frequency of the brightness change information is not more than the predetermined value.

[Supplementary Note 11]

The living body determination device according to Supplementary Note 10, wherein the predetermined frequency is within a range of 0.5 Hz to 3 Hz.

[Supplementary Note 12]

The living body determination device according to any one of Supplementary Notes 1 to 11, wherein the control unit acquires the first spectroscopic information about a predetermined region of a first image indicated by the first image information and acquires the second spectroscopic information about a predetermined region of a second image indicated by the second image information, and the predetermined region of the first image matches the predetermined region of the second image.

[Supplementary Note 13]

The living body determination device according to any one of Supplementary Notes 1 to 11, wherein the control unit acquires the first spectroscopic information about a predetermined region of a first image indicated by the first image information, and acquires the second spectroscopic information about a predetermined region of a second image indicated by the second image information, and the predetermined region of the first image is different from the predetermined region of the second image.

[Supplementary Note 14]

The living body determination device according to any one of Supplementary Notes 1 to 13, wherein the predetermined spectral characteristic is a combination of spectra of a plurality of components related to a living body.

[Supplementary Note 15]

A living body determination method that is performed by a device, the device comprising: a pedestal for placing a measurement target; a spectroscopic means that receives light entering from the pedestal side and disperses the light into intensities corresponding to wavelengths and outputs it; a first light emission means that is provided at a position facing the spectroscopic means with the pedestal therebetween and emits first light having a plurality of spectra toward the pedestal; a second light emission means that emits second light having a plurality of spectra toward the pedestal from the spectroscopic means side; and an image acquisition means that receives light output from the spectroscopic means and outputs image information indicating brightness corresponding to an intensity of the light, the method:

acquiring first image information related to the measurement target from the image acquisition means for each spectrum of the first light and acquiring first spectroscopic information based on each first image information, acquiring second image information related to the measurement target from the image acquisition means for each spectrum of the second light and acquiring second spectroscopic information based on each second image information; and determining whether or not the measurement target is a living body based on comparison results between each of the first and second spectroscopic information and a predetermined spectral characteristic.

[Supplementary Note 16]

A program that causes a computer of a device comprising: a pedestal for placing a measurement target; a spectroscopic means that receives light entering from the pedestal side and disperses the light into intensities corresponding to wavelengths and outputs it; a first light emission means that is provided at a position facing the spectroscopic means with the pedestal therebetween and emits first light having a plurality of spectra toward the pedestal; a second light emission means that emits second light having a plurality of spectra toward the pedestal from the spectroscopic means side; and an image acquisition means that receives light output from the spectroscopic means and outputs image information indicating brightness corresponding to an intensity of the light, to execute:

a process of acquiring first image information related to the measurement target from the image acquisition means for each spectrum of the first light and acquiring first spectroscopic information based on each first image information;

a process of acquiring second image information related to the measurement target from the image acquisition means for each spectrum of the second light and acquiring second spectroscopic information based on each second image information; and a process of determining whether or not the measurement target is a living body based on comparison results between each of the first and second spectroscopic information and a predetermined spectral characteristic.

[Supplementary Note 17]

A biometric authentication device comprising:

a pedestal for placing a measurement target;

a spectroscopic means that receives light entering from the pedestal side and disperses the light into intensities corresponding to wavelengths and outputs it;

a first light emission means that is provided at a position facing the spectroscopic means with the pedestal therebetween and emits first light having a plurality of spectra toward the pedestal;

a second light emission means that emits second light having a plurality of spectra toward the pedestal from the spectroscopic means side;

an image acquisition means that receives light output from the spectroscopic means and outputs image information indicating brightness corresponding to an intensity of the light; and an image processing unit that acquires first image information related to the measurement target from the image acquisition means for each spectrum of the first light and acquires first spectroscopic information based on each first image information, the image processing unit acquiring second image information related to the measurement target from the image acquisition means for each spectrum of the second light and acquiring, based on each second image information, second spectroscopic information and biometric information, the biometric information indicating depressions and protrusions on a surface of the measurement target;

a living body authenticity determination unit that determines whether or not the measurement target is a living body based on comparison results between each of the first and second spectroscopic information and a predetermined spectral characteristic; and a biometric authentication unit that determines whether or not the biometric information matches preliminarily registered authentication biometric information in a case where the measurement target is determined as a living body, the biometric authentication unit determining a successful authentication in a case where they are matched, and the biometric authentication unit determining an authentication error in a case where they are not matched.

[Supplementary Note 18]

The biometric authentication device according to Supplementary Note 17, wherein the living body authenticity determination unit determines whether or not the measurement target is a living body based on a correlation degree between each of the first and second spectroscopic information and the predetermined spectral characteristic.

[Supplementary Note 19]

The biometric authentication device according to Supplementary Note 17 or 18, wherein a wavelength band of the first light emission means and a wavelength band of the second light emission means are within a range from a visible light range to a near-infrared light range.

[Supplementary Note 20]

The biometric authentication device according to any one of Supplementary Notes 17 to 19, wherein a wavelength band of the first light emission means and a wavelength band of the second light emission means are within a range of 400 to 1000 nm.

[Supplementary Note 21]

The biometric authentication device according to Supplementary Notes 17 to 20, wherein, in a state where the first light emission means is turned on and the second light emission means is turned off, the image processing unit acquires the first image information from the image acquisition means, and in a state where the second light emission means is turned on and the first light emission means is turned off, the image processing unit acquires the second image information from the image acquisition means.

[Supplementary Note 22]

The biometric authentication device according to any one of Supplementary Notes 17 to 20, wherein a wavelength band of the first light emission means is set to a longer wavelength band than a wavelength band of the second light emission means, and in a state where the first and second light emission means are both turned on, the image processing unit acquires the first and second image information from the image acquisition means.

[Supplementary Note 23]

The biometric authentication device according to Supplementary Note 22, wherein a wavelength band of the first light emission means is 550 to 1000 nm, and a wavelength band of the second light emission means is 400 to 600 nm.

[Supplementary Note 24]

The biometric authentication device according to any one of Supplementary Notes 17 to 20, wherein the spectroscopic means comprises:

a first spectroscopic device that is positioned on an optical axis of the first light emission means and receives transmitted light based on the first light from the measurement target; and a second spectroscopic device that is provided in a position facing the second light emission means with the optical axis therebetween and receives reflected light based on the second light from the measurement target, and the image acquisition means comprises:

a first image acquisition device that receives light output from the first spectroscopic means and outputs image information indicating brightness corresponding to an intensity of the light; and a second image acquisition device that receives light output from the second spectroscopic means and outputs image information indicating brightness corresponding to an intensity of the light, and in a state where the first and second light emission means are both turned on, the image processing unit acquires the first image information from the first image acquisition device and acquires the second image information from the second image acquisition device.

[Supplementary Note 25]

The biometric authentication device according to any one of Supplementary Notes 17 to 20, further comprising:

a first polarization control device that is provided between the second light emission means and the pedestal, the first polarization control device controlling a polarization state of the second light into a predetermined polarization; and a second polarization control device that is provided between the spectroscopic means and the pedestal, the second polarization control device controlling a polarization state of light entering from the pedestal side, and the second polarization control device being capable of switching between a first polarization control state where a first polarization is output and a second polarization control state where a second polarization orthogonal to the first polarization is output, wherein in a state where the first and second light emission means are both turned on, the image processing unit switches the second polarization control device into the first polarization control state and acquires the first image information from the image acquisition means, and switches the second polarization control device into the second polarization control state and acquires the second image information from the image acquisition means.

[Supplementary Note 26]

The biometric authentication device according to any one of Supplementary Notes 17 to 25, wherein the image processing unit calculates brightness change information indicating temporal changes in brightness, based on the first image information, and the living body authenticity determination unit determines that the measurement target has a pulse wave in a case where amplitude at a predetermined frequency of the brightness change information is higher than a predetermined value, and the living body authenticity determination unit determines that the measurement target does not have a pulse wave in a case where amplitude at the predetermined frequency of the brightness change information is not more than the predetermined value.

[Supplementary Note 27]

The biometric authentication device according to Supplementary Note 26, wherein the predetermined frequency is within a range of 0.5 Hz to 3 Hz.

[Supplementary Note 28]

The biometric authentication device according to any one of Supplementary Notes 17 to 27, wherein the image processing unit acquires the first spectroscopic information about a predetermined region of a first image indicated by the first image information, and acquires the second spectroscopic information about a predetermined region of a second image indicated by the second image information, and the predetermined region of the first image matches the predetermined region of the second image.

[Supplementary Note 29]

The biometric authentication device according to any one of Supplementary Notes 17 to 27, wherein the image processing unit acquires the first spectroscopic information about a predetermined region of a first image indicated by the first image information, and acquires the second spectroscopic information about a predetermined region of a second image indicated by the second image information, and the predetermined region of the first image is different from the predetermined region of the second image.

[Supplementary Note 30]

The biometric authentication device according to any one of Supplementary Notes 17 to 29, wherein the predetermined spectral characteristic is a combination of spectra of a plurality of components related to a living body.

[Supplementary Note 31]

A biometric authentication method that is performed by a device, the device comprising: a pedestal for placing a measurement target; a spectroscopic means that receives light entering from the pedestal side and disperses the light into intensities corresponding to wavelengths and outputs it; a first light emission means that is provided at a position facing the spectroscopic means with the pedestal therebetween and emits first light having a plurality of spectra toward the pedestal; a second light emission means that emits second light having a plurality of spectra toward the pedestal from the spectroscopic means side; and an image acquisition means that receives light output from the spectroscopic means and outputs image information indicating brightness corresponding to an intensity of the light, the method:

acquiring first image information related to the measurement target from the image acquisition means for each spectrum of the first light and acquiring first spectroscopic information based on each first image information;

acquiring second image information related to the measurement target from the image acquisition means for each spectrum of the second light and acquiring, based on each second image information, second spectroscopic information and biometric information, the biometric information indicating depressions and protrusions on a surface of the measurement target;

determining whether or not the measurement target is a living body based on comparison results between each of the first and second spectroscopic information and a predetermined spectral characteristic; and determining whether or not the biometric information matches preliminarily registered authentication biometric information in a case where the measurement target is determined as a living body, determining a successful authentication in a case where they are matched, and determining an authentication error in a case where they are not matched.

[Supplementary Note 32]

A program that causes a computer of a device comprising: a pedestal for placing a measurement target; a spectroscopic means that receives light entering from the pedestal side and disperses the light into intensities corresponding to wavelengths and outputs it; a first light emission means that is provided at a position facing the spectroscopic means with the pedestal therebetween and emits first light having a plurality of spectra toward the pedestal; a second light emission means that emits second light having a plurality of spectra toward the pedestal from the spectroscopic means side; and an image acquisition means that receives light output from the spectroscopic means and outputs image information indicating brightness corresponding to an intensity of the light, to execute:

a process of acquiring first image information related to the measurement target from the image acquisition means for each spectrum of the first light and acquiring first spectroscopic information based on each first image information;

a process of acquiring second image information related to the measurement target from the image acquisition means for each spectrum of the second light and acquiring, based on each second image information, second spectroscopic information and biometric information, the biometric information indicating depressions and protrusions on a surface of the measurement target;

a process of determining whether or not the measurement target is a living body based on comparison results between each of the first and second spectroscopic information and a predetermined spectral characteristic; and a process of determining whether or not the biometric information matches preliminarily registered authentication biometric information in a case where the measurement target is determined as a living body, determining a successful authentication in a case where they are matched, and determining an authentication error in a case where they are not matched.

According to the present invention described above, determination of a living body can be accurately performed and a film-shaped forged fingerprint fragment can also be detected without inviting an increase in the size of the device and an increase in the number of components.

Furthermore, according to the present invention, it is possible to improve reliability of biometric authentication and ensure a high level of security.

The present invention has been described with reference to the exemplary embodiments. However, the present invention is not limited to the exemplary embodiments described above. Various modifications that can be understood by those skilled in the art may be made to the configuration and operation of the present invention, without departing from the scope of the invention.

This application is based upon and claims the benefit of priority from Japanese patent application No. 2015-184188, filed Sep. 17, 2015, the disclosure of which is incorporated herein in its entirety by reference.

REFERENCE SYMBOLS 1, 11 Control unit
1a, 11a Image processing unit
1b, 11b Living body authenticity determination unit
2 Memory
3 Input unit
4 Display unit
10 Living body determination device
11c Biometric authentication unit
101, 102 Light emission device
103 Measurement target placement device
104 Spectroscopic device
105 Image acquisition device
106 Calculation device

What is claimed is:

1. A living body determination device comprising:
a pedestal for placing a measurement target;
a spectroscopic device that receives light entering from the pedestal side and disperses the light into intensities corresponding to wavelengths and outputs it;
a first light emission device that is provided at a position facing the spectroscopic device with the pedestal therebetween and emits first light having a plurality of spectra toward the pedestal;
a second light emission device that emits second light having a plurality of spectra toward the pedestal from the spectroscopic device side;
an image acquisition device that receives light output from the spectroscopic device and outputs image information indicating brightness corresponding to an intensity of the light; and a control unit that acquires first image information related to the measurement target from the image acquisition device for each spectrum of the first light and acquires first spectroscopic information based on each first image information, the control unit acquiring second image information related to the measurement target from the image acquisition device for each spectrum of the second light and acquiring second spectroscopic information based on each second image information, and the control unit determining whether or not the measurement target is a living body based on comparison results between each of the first and second spectroscopic information and a predetermined spectral characteristic.

2. The living body determination device according to claim 1, wherein the control unit determines whether or not the measurement target is a living body based on a correlation degree between each of the first and second spectroscopic information and the predetermined spectral characteristic.

3. The living body determination device according to claim 1, wherein, in a state where the first light emission device is turned on and the second light emission device is turned off, the control unit acquires the first image information from the image acquisition device, and in a state where the second light emission device is turned on and the first light emission device is turned off, the control unit acquires the second image information from the image acquisition device.

4. The living body determination device according to claim 1,
wherein a wavelength band of the first light emission device is set to a longer wavelength band than a wavelength band of the second light emission device, and
in a state where the first and second light emission devices are both turned on, the control unit acquires the first and second image information from the image acquisition device.

5. The living body determination device according to claim 1,
wherein the spectroscopic comprises:
a first spectroscopic device that is positioned on an optical axis of the first light emission device and receives transmitted light based on the first light from the measurement target; and
a second spectroscopic device that is provided in a position facing the second light emission device with the optical axis therebetween and receives reflected light based on the second light from the measurement target, and
the image acquisition device comprises:
a first image acquisition device that receives light output from the first spectroscopic device and outputs image information indicating brightness corresponding to an intensity of the light; and
a second image acquisition device that receives light output from the second spectroscopic device and outputs image information indicating brightness corresponding to an intensity of the light, and
in a state where the first and second light emission devices are both turned on, the control unit acquires the first image information from the first image acquisition device and acquires the second image information from the second image acquisition device.

6. The living body determination device according to claim 1, further comprising:

a first polarization control device that is provided between the second light emission device and the pedestal, the first polarization control device controlling a polarization state of the second light into a predetermined polarization; and a second polarization control device that is provided between the spectroscopic device and the pedestal, the second polarization control device controlling a polarization state of light entering from the pedestal side, and the second polarization control device being capable of switching between a first polarization control state where a first polarization is output and a second polarization control state where a second polarization orthogonal to the first polarization is output, wherein in a state where the first and second light emission devices are both turned on, the control unit switches the second polarization control device into the first polarization control state and acquires the first image information from the image acquisition device, and switches the second polarization control device into the second polarization control state and acquires the second image information from the image acquisition device.

7. The living body determination device according to claim 1, wherein the control unit calculates brightness change information indicating temporal changes in brightness, based on the first image information, the control unit determines that the measurement target has a pulse wave in a case where amplitude at a predetermined frequency of the brightness change information is higher than a predetermined value, and the control unit determines that the measurement target does not have a pulse wave in a case where amplitude at the predetermined frequency of the brightness change information is not more than the predetermined value.

8. The living body determination device according to claim 1, wherein the control unit acquires the first spectroscopic information about a predetermined region of a first image indicated by the first image information and acquires the second spectroscopic information about a predetermined region of a second image indicated by the second image information, and the predetermined region of the first image matches the predetermined region of the second image.

9. The living body determination device according to claim 1, wherein the control unit acquires the first spectroscopic information about a predetermined region of a first image indicated by the first image information, and acquires the second spectroscopic information about a predetermined region of a second image indicated by the second image information, and the predetermined region of the first image is different from the predetermined region of the second image.

10. The living body determination device according to claim 1, wherein the predetermined spectral characteristic is a combination of spectra of a plurality of components related to a living body.

11. A living body determination method that is performed by a device, the device comprising: a pedestal for placing a measurement target; a spectroscopic device that receives light entering from the pedestal side and disperses the light into intensities corresponding to wavelengths and outputs it; a first light emission device that is provided at a position facing the spectroscopic device with the pedestal therebetween and emits first light having a plurality of spectra toward the pedestal; a second light emission device that emits second light having a plurality of spectra toward the pedestal from the spectroscopic device side; and an image acquisition device that receives light output from the spectroscopic device and outputs image information indicating brightness corresponding to an intensity of the light, the method comprising:

acquiring first image information related to the measurement target from the image acquisition device for each spectrum of the first light;

acquiring first spectroscopic information based on each first image information;

acquiring second image information related to the measurement target from the image acquisition device for each spectrum of the second light;

acquiring second spectroscopic information based on each second image information; and determining whether or not the measurement target is a living body based on comparison results between each of the first and second spectroscopic information and a predetermined spectral characteristic.

12. A non-transitory computer readable recording medium storing a program for a computer of a device, the device comprising: a pedestal for placing a measurement target; a spectroscopic device that receives light entering from the pedestal side and disperses the light into intensities corresponding to wavelengths and outputs it; a first light emission device that is provided at a position facing the spectroscopic device with the pedestal therebetween and emits first light having a plurality of spectra toward the pedestal; a second light emission device that emits second light having a plurality of spectra toward the pedestal from the spectroscopic device side; and an image acquisition device that receives light output from the spectroscopic device and outputs image information indicating brightness corresponding to an intensity of the light, the program causing the computer to execute:

acquiring first image information related to the measurement target from the image acquisition device for each spectrum of the first light;

acquiring first spectroscopic information based on each first image information;

acquiring second image information related to the measurement target from the image acquisition device for each spectrum of the second light;

acquiring second spectroscopic information based on each second image information; and determining whether or not the measurement target is a living body based on comparison results between each of the first and second spectroscopic information and a predetermined spectral characteristic.

* * * * *